US008273867B2

(12) United States Patent
Dowdy et al.

(10) Patent No.: US 8,273,867 B2
(45) Date of Patent: Sep. 25, 2012

(54) TRANSDUCIBLE DELIVERY OF SIRNA BY DSRNA BINDING DOMAIN FUSIONS TO PTD/CPPS

(75) Inventors: Steven F. Dowdy, La Jolla, CA (US); Jehangir S. Wadia, San Diego, CA (US); Bryan Meade, San Diego, CA (US); Akiko Eguchi, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 265 days.

(21) Appl. No.: 12/278,739

(22) PCT Filed: Feb. 9, 2007

(86) PCT No.: PCT/US2007/003641
§ 371 (c)(1),
(2), (4) Date: Dec. 10, 2008

(87) PCT Pub. No.: WO2007/095152
PCT Pub. Date: Aug. 23, 2007

(65) Prior Publication Data
US 2009/0093026 A1    Apr. 9, 2009

Related U.S. Application Data

(60) Provisional application No. 60/772,787, filed on Feb. 10, 2006, provisional application No. 60/775,638, filed on Feb. 21, 2006.

(51) Int. Cl.
*C12N 15/11* (2006.01)
*C07H 21/02* (2006.01)
(52) U.S. Cl. ............ 536/24.5; 514/44 A; 530/300
(58) Field of Classification Search .............. None
See application file for complete search history.

(56) References Cited

U.S. PATENT DOCUMENTS

| 4,888,278 | A |   | 12/1989 | Singer et al. |
| 5,489,525 | A | * | 2/1996 | Pastan .................... 435/7.23 |
| 5,547,932 | A |   | 8/1996 | Curiel et al. |
| 5,652,122 | A |   | 7/1997 | Frankel et al. |
| 5,670,617 | A |   | 9/1997 | Frankel et al. |
| 5,674,980 | A |   | 10/1997 | Frankel et al. |
| 5,747,641 | A |   | 5/1998 | Frankel et al. |
| 5,804,604 | A |   | 9/1998 | Frankel et al. |
| 6,022,735 | A |   | 2/2000 | Curiel et al. |
| 6,077,663 | A |   | 6/2000 | Curiel et al. |
| 6,221,355 | B1 |   | 4/2001 | Dowdy et al. |
| 6,309,663 | B1 |   | 10/2001 | Patel et al. |
| 6,316,003 | B1 |   | 11/2001 | Frankel et al. |
| 6,348,185 | B1 |   | 2/2002 | Piwnica-Worms et al. |
| 6,376,248 | B1 |   | 4/2002 | Hawley-Nelson et al. |
| 6,423,334 | B1 |   | 7/2002 | Brayden et al. |
| 6,468,986 | B1 |   | 10/2002 | Zuckermann et al. |
| 6,645,501 | B2 |   | 11/2003 | Dowdy et al. |
| 6,835,810 | B2 |   | 12/2004 | Hwu |
| 6,841,535 | B2 |   | 1/2005 | Divita et al. |
| 6,903,077 | B1 |   | 6/2005 | Heintz |
| 7,084,248 | B2 |   | 8/2006 | Summerton |
| 7,101,844 | B2 |   | 9/2006 | Kim et al. |
| 7,166,692 | B2 |   | 1/2007 | Karas |
| 7,297,759 | B2 |   | 11/2007 | Park et al. |
| 7,329,638 | B2 | * | 2/2008 | Yang et al. ................ 424/185.1 |
| 7,354,737 | B2 |   | 4/2008 | Lee et al. |
| 7,420,031 | B2 |   | 9/2008 | Karas |
| 7,491,805 | B2 |   | 2/2009 | Vargeese et al. |
| 7,514,530 | B2 |   | 4/2009 | Divita et al. |
| 7,585,834 | B2 |   | 9/2009 | Wender et al. |
| 7,807,780 | B2 | * | 10/2010 | Waugh et al. ................ 530/327 |
| 2003/0125242 | A1 | * | 7/2003 | Rosenecker et al. ............ 514/8 |
| 2004/0127441 | A1 | * | 7/2004 | Gleave et al. ................ 514/44 |
| 2004/0204377 | A1 |   | 10/2004 | Rana |
| 2005/0032186 | A1 | * | 2/2005 | Kim et al. .................... 435/199 |
| 2005/0042603 | A1 |   | 2/2005 | Wang |
| 2005/0074884 | A1 |   | 4/2005 | Robbins et al. |
| 2005/0147993 | A1 |   | 7/2005 | Khan |
| 2005/0196414 | A1 | * | 9/2005 | Dake et al. ................ 424/239.1 |
| 2005/0239687 | A1 |   | 10/2005 | Divita et al. |
| 2005/0260756 | A1 |   | 11/2005 | Troy et al. |
| 2006/0030003 | A1 | * | 2/2006 | Simon .................... 435/69.1 |
| 2006/0035815 | A1 |   | 2/2006 | Chen et al. |
| 2006/0040882 | A1 |   | 2/2006 | Chen et al. |
| 2006/0178297 | A1 |   | 8/2006 | Troy et al. |

(Continued)

FOREIGN PATENT DOCUMENTS

WO    2000040723 A2    7/2000

(Continued)

OTHER PUBLICATIONS

Ryter and Schultz (EMBO J. 17(24): 7505-7513, 1998).*
Carpick et al (J. Biol. Chem. 272(14): 9510-9516, 1997).*
Fittipaldi et al (Adv. Drug. Deliv. Rev. 57: 597-608, 2005).*
Rudolph et al (J. Biol. Chem. 278(13): 11411-11418, 2003).*
Torchilin et al (Proc. Nat. Acad. Sci. USA, 98(15): 8786-8791, 2001).*
Chauhan et al., "PTD-Fusion Peptide as a Delivery Vehicle for SiRNA to Target HIV Reservoirs", Molecular Therapy, Academic Press, San Diego, CA, US, Jan. 1, 2006, vol. 13., p. S277.
Grotzinger, Thilo, Supplementary European Search Report, Date of Completion of Search: Jan. 26, 2010, Application No. EP07750474.
Scherr et al., "Gene silencing mediated by small interfering RNAs in mammalian cells," Current Medicinal Chemistry, Feb. 2003, pp. 245-256, vol. 10, No. 3.

(Continued)

*Primary Examiner* — Richard Schnizer
(74) *Attorney, Agent, or Firm* — Joseph R. Baker, Jr.; Gavrilovich, Dodd & Lindsey LLP

(57) ABSTRACT

The disclosure provides fusion polypeptides and constructs useful in delivering anionically charged nucleic acid molecules including diagnostics and therapeutics to a cell or subject. The fusion constructs include a protein transduction domain and a nucleic acid binding domain, or a protein transduction domain and a nucleic acid that is coated with one or more nucleic acid binding domains sufficient to neutralize an anionic charge on the nucleic acid. Also provided are methods of treating disease and disorders such as cell proliferative disorders.

30 Claims, 7 Drawing Sheets

U.S. PATENT DOCUMENTS

| | | |
|---|---|---|
| 2006/0182736 A1 | 8/2006 | Kim et al. |
| 2006/0205665 A1 | 9/2006 | Bonny |
| 2006/0222657 A1 | 10/2006 | Dowdy et al. |
| 2008/0027025 A1 | 1/2008 | Dowdy et al. |
| 2008/0153737 A1 | 6/2008 | Lieberman et al. |
| 2009/0093425 A1 | 4/2009 | Dowdy et al. |
| 2009/0098049 A1 | 4/2009 | Dowdy et al. |

FOREIGN PATENT DOCUMENTS

| | | |
|---|---|---|
| WO | 2004007721 A1 | 1/2004 |
| WO | 2004048545 A2 | 6/2004 |
| WO | 2005084158 A2 | 9/2005 |
| WO | 2008008476 A2 | 1/2008 |
| WO | 2010129853 A3 | 11/2010 |
| WO | 2010141471 A3 | 12/2010 |

OTHER PUBLICATIONS

Baharlou, Simin, International Preliminary Report on Patentability and Written Opinion, Date of Issuance of Report: Jan. 13, 2009, International Application No. PCT/US07/15966.

Barka et al., "Transduction of TAT-HA-Beta-galactosidase Fusion Protein into Salivary Gland-derived Cells and Organ Cultures of the Devolping Gland, and into Rat Submandibular Gland in Vivo", The Journal of Histochemistry and Cytochemistry, 2000, vol. 48, No. 11, pp. 1453-1460.

Bell-Harris Valerie. Written Opinion of the International Search Authority (US) for International Application No. PCT/US2007/15966. Date mailed Jun. 16, 2008.

Desai, Anand, International Search Report, Date of Mailing of Report: Jun. 1, 2007, International Application No. PCT/US04/20837.

Falnes et al., "Ability of the Tat basic domain and VP22 to mediate cell binding, but not membrane translocation of the diptheria toxin A-fragment", Biochemistry 40: 4349-4358 (2001).

Li, Fang. Office Action issued by the China State Intellectual Property Office for Application No. 200780030587.9 PCT/US2007/015966.

Linder, Nora, International Preliminary Report on Patentability and Written Opinion, Date of Issuance of Report: Jun. 19, 2007, International Application No. PCT/US04/20837.

Martin, Molly et al., "Peptide-guided Gene Delivery", The AAPS Journal 2007; 9 (1), E18-E29.

Michiue, Hiroyuki et al., "The NH2 Terminus of Influenza Virus Hemagglutinin-2 Subunit Peptides Enhances the Antitumor Potency of Polyarginine-meidated p53 Protein Transduction", The Journal of Biological Chemistry, vol. 280, No. 9, pp. 8285-8289, (2004).

Navarro-Quiroga et al., "Improved neurotensin-vector-mediated gene transfer by the coupling of hemagglutinin HA2 fusogenic peptide and Vp1 SV40 nuclear localization signal", Molecular Brain Research 105: 86-97 (2002).

Robinson, Hope A. US Nonfinal Office action for 11/662,170. Mail Date Feb. 18, 2010.

Swartz, Rodney P. US Nonfinal Office action for U.S. Appl. No. 11/661,239. Mail Date Sep. 18, 2009.

Swartz, Rodney P. US Final Office action for U.S. Appl. No. 11/661,239. Mail Date Feb. 26, 2010.

Swartz, Rodney P. US Nonfinal Office action for U.S. Appl. No. 11/661,239. Mail Date Jun. 03, 2010.

Takenobu et al., "Development of p53 protein transduction therapy using membrane-permeable peptides and the application to oral cancer cells", Molecular Cancer Therapeutics 1: 1043-1049 (2002).

Violini et al., "Evidence for a plasma membrane-mediated permeability barrier to Tat basic domain in well-differentiated epithelial cells: lack of correlation with heparan sulfate", Biochemistry 41: 12652-12661 (2002).

Xia et al., "The HIV Tat protein transduction domain improves the biodistribution of beta-glucuronidase expressed from recombinant viral vectors." Nature Biotechnology 19: 640-644 (2001).

Yang et al., "HIV-1 TAT-mediated protein transduction and subcellular localiztion using novel expression vector", FEBS Letters 532: 36-44 (2002).

Robinson, Hope. Final Office Action for U.S. Appl. No. 11/662,170. United States Patent and Trademark Office. Mail Date 7/2/10.

Park et al., "9-Polylysine Protein Transduction Domain: Enhanced Penetration Efficiency of Superoxide Dismutase into Mammalian Cells and Skin," Mol. Cells 13(2): pp. 202-208 (Apr. 2002).

Rudolph et al. "Oligomers of the Arginine-rich Motif of the HIV-1 TAT Protein Are Capable of Transferring Plasmid DNA into Cells," J. Biol. Chem. 278(13): 11411-11418 (2003).

Astriab-Fisher et al "Conjugates of antisense oligonucleotides with the Tat and antennapedia cell-penetrating peptides: effects on cellular uptake, binding to target sequences, and biologic actions," Pharm. Res. 19(6): 744-754 (2002).

* cited by examiner

TRANSDUCIBLE DELIVERY OF SIRNA BY DSRNA BINDING DOMAIN FUSIONS TO PTD/CPPS

CROSS-REFERENCE TO RELATED APPLICATIONS

This application is filed under 35 U.S.C. §371 and claims priority to International Application No. PCT/US07/03641, filed Feb. 9, 2007, which application claims priority under 35 U.S.C. §119 to U.S. Provisional Application Ser. No. 60/772,787, filed Feb. 10, 2006; and U.S. Provisional Application Ser. No. 60/775,638, filed Feb. 21, 2006, the disclosures of which are incorporated herein by reference.

STATEMENT REGARDING FEDERAL SPONSORED RESEARCH

The U.S. Government has certain rights in this invention pursuant to Grant No. RO0 CA96098 from the National Institutes of Health.

FIELD OF THE INVENTION

The invention relates to nucleic acid delivery to cells. More particularly, the invention relates to delivery of anionically charged molecules such as siRNA to cells using a protein transduction domain fused to a nucleic acid binding domain that neutralizes the anionic charge.

BACKGROUND

The discovery of RNA interference (RNAi) as a cellular mechanism that selectively degrades mRNAs allows for both the targeted manipulation of cellular phenotypes in cell culture and the potential for development of directed therapeutics (Behlke, Mol. Ther. 13, 644-670, 2006; Xie et al., Drug Discov. Today 11, 67-73, 2006).

Although siRNAs have great potential for manipulation of cellular phenotypes, due to their size and negative (anionic) charged nature, siRNAs are macromolecules with no ability to enter cells. Indeed, siRNAs are 25× in excess of Lipinski's "Rule of 5s" for cellular delivery of membrane diffusible molecules that generally limits size to less than 500 Da. Consequently, in the absence of a delivery vehicle or transfection agent, naked siRNAs do not enter cells, even at millimolar concentrations (Barquinero et al., Gene Ther. 11 Suppl 1, S3-9, 2004). Significant attention has been focused on the use of cationic lipids that both condense the siRNA and punch holes in the cellular membrane to solve the siRNA delivery problem. Although widely used, transfection reagents fail to achieve efficient delivery into many cell types, especially primary cells and hematopoetic cell lineages (T and B cells, macrophage). Moreover, lipofection reagents often result in varying degrees of cytotoxicity ranging from mild in tumor cells to high in primary cells.

Recent cell-directed targeting approaches of antibody fusions to DNA condensing protamine (Song et al., Nat. Biotechnol. 23, 709-717, 2005) and siRNA fusions to receptor targeted RNA aptamers (McNamara et al., Nat. Biotechnol. 24, 1005-1015, 2006) offer the potential to delivery siRNAs into select cells. While both approaches are promising, they fail to deliver siRNAs into 100% of tumor cells expressing the receptor, are not easily amendable to other non-receptor expressing cells, and have only been tested on a couple of cell types. Lastly, induction of aggregates to form nanoparticles by inclusion of cholesterol to form LDL particles and PEI condensation approaches or siRNA encapsulation in liposomes to mask the negative charge have been shown to deliver siRNAs with varying degrees of success into some tumor cells (Scherr et al., Ann. Hematol. 83, 1-8, 2004; Schiffelers et al., Nucleic Acids Res. 32, e149, 2004; Song et al., 2005; Soutschek et al., Nature 432, 173-178, 2004; Urban-Klein et al., Gene Ther. 12, 461-466, 2005; Zhang et al., Genet. Vaccines Ther. 3, 5, 2005). Thus, devising an approach to solve the siRNA macromolecular delivery problem that targets ~100% of all cell types, primary and tumorigenic, by a rapid, non-cytotoxic mechanism remains important for expansion of RNAi potential in cell culture, target screening and therapeutic development.

SUMMARY

The invention provides a composition comprising a nucleic acid binding protein in complex with an anionically charged nucleic acid to form a nucleic acid binding protein-nucleic acid complex; and a protein transduction domain (PTD) linked to the nucleic acid binding protein-nucleic acid complex. In one aspect, the nucleic acid binding protein comprises a double stranded RNA binding domain (DRBD). In another aspect, the nucleic acid is an anionically charged nucleic acid. In yet another aspect, the nucleic acid comprises a dsRNA.

The invention further provides a composition comprising a fusion polypeptide comprising: i) a first domain comprising a protein transduction moiety (PTD), the transduction moiety comprising a membrane transport function; and ii) a second domain comprising a nucleic acid binding protein; b) a nucleic acid, wherein the nucleic acid is anionically charged and interacts with the nucleic acid binding protein and wherein the overall anionic charge of the PTD-nucleic acid binding protein-nucleic acid is reduced relative to the nucleic acid alone; and c) a pharmaceutically acceptable carrier.

The invention provides a fusion polypeptide comprising: a) a protein transduction domain (PTD), the transduction domain comprising a membrane transport function; and b) a nucleic acid binding domain that neutralizes or reduces anionic charges of an associated nucleic acid, wherein the PTD is operably linked to the nucleic acid binding domain.

The invention also includes a pharmaceutical composition comprising a) a protein transduction domain (PTD), the transduction domain comprising a membrane transport function; and b) a nucleic acid binding domain that neutralizes or reduces anionic charges of an associated nucleic acid, wherein the PTD is operably linked to the nucleic acid binding domain and a pharmaceutically acceptable carrier.

The invention provides a method of introducing an anionically charged nucleic acid molecule into a cell comprising contacting the cell with a composition comprising a nucleic acid binding protein in complex with an anionically charged nucleic acid to form a nucleic acid binding protein-nucleic acid complex, and a protein transduction domain (PTD) linked to the nucleic acid binding protein-nucleic acid complex; or a fusion polypeptide comprising a) a protein transduction domain (PTD), the transduction domain comprising a membrane transport function; and b) a nucleic acid binding domain that neutralizes or reduces anionic charges of an associated nucleic acid, wherein the PTD is operably linked to the nucleic acid binding domain and an associated nucleic acid.

The invention further provides a method of introducing an anionically charged nucleic acid molecule into a cell comprising associating the nucleic acid molecule with a nucleic acid binding domain to neutralize or reduce the anionic charge and linking the complex to a protein transduction domain (PTD) and contacting the cell with the PTD-charge neutralized nucleic acid.

The invention also provides an isolated polynucleotide encoding the fusion polypeptide comprising a) a protein transduction domain (PTD), the transduction domain comprising a membrane transport function; and b) a nucleic acid binding domain that neutralizes or reduces anionic charges of an associated nucleic acid, wherein the PTD is operably linked to the nucleic acid binding domain. A vector comprising the polynucleotide as well as host cells comprising the vector and/or polynucleotide are also provided.

The invention provides a method of producing a fusion polypeptide, comprising expressing a polynucleotide of the invention and substantially purifying the expressed fusion polypeptide.

The invention also provides a method of producing a fusion polypeptide, comprising culturing a host cell containing a polynucleotide or vector of the invention under conditions whereby the polynucleotide is expressed and substantially purifying the expressed fusion polypeptide.

The invention provides a method of making a composition for transducing a cell, comprising contacting an anionically charged nucleic acid with a fusion polypeptide comprising a) a protein transduction domain (PTD), the transduction domain comprising a membrane transport function; and b) a nucleic acid binding domain that neutralizes or reduces anionic charges of an associated nucleic acid, wherein the PTD is operably linked to the nucleic acid binding domain.

The invention also provides a kit comprising a vessel or vessels containing (a) a protein transduction domain; and (b) a nucleic acid binding protein. The kit may further comprise a dsRNA molecule.

The invention provides methods and compositions useful to deliver siRNA into cells by reversibly masking or neutralizing the charge on polynucleotides using protein transduction domains (PTDs). In one aspect double stranded RNA (dsRNA) binding domains (DRBDs) are used to mask the charge. In a further aspect, two to four DRBDs cover the surface of the dsRNA cylinder and mask a substantial portion of the polynucleotide to be delivered. DRBDs bind in a sequence independent manner, so that any polynucleotide (e.g., siRNA) will be able to be delivered by the methods and compositions of the invention.

The disclosure provides fusion polypeptides and constructs useful in delivering anionically charged nucleic acid molecules including diagnostics and therapeutics to a cell or subject. The fusion constructs include a protein transduction domain and a nucleic acid binding domain, or a protein transduction domain and a nucleic acid that is coated with one or more nucleic acid binding domains sufficient to neutralize an anionic charge on the nucleic acid.

For example, charge neutralization of the anionic RNA frees the cationic PTD and also prevents aggregation of the conjugate. The exposed PTD interacts with the cell surface, induces macropinocytosis and promotes escape from the macropinosome into the cytoplasm. Once inside the cell, the nucleic acid binding protein (e.g., DRBD) is either removed by, for example, endogenous DRBD containing proteins, such as TRBP which is involved in loading siRNAs into the RISC, or a destabilizing motif, such as PEST sequence, could be added, allowing for removal from the siRNA in the cytoplasm.

(red), Alexa488-conjugated anti-SSEA-4 (green). Genomic DNA, Hoechst (blue). (E) Immunohistochemistry analysis of GATA6 and SSEA4 expression in HUES9 hESCs at 10 days post-treatment with PTD-DRB delivered Oct4 or Luciferase (Luc) siRNAs. Antibodies: Alexa594-conjugated anti-GATA6 (red), Alexa488-conjugated anti-SSEA-4 (green). Genomic DNA, Hoechst (blue).

FIG. 6A-D shows cytotoxicity. (A-D) Cells, as indicated, treated with mock, lipofection or PTD-DRBD plus siRNAs, as indicated, were analyzed by flow cytometry forward scatter (FSC) and side scatter (SSC) for cytotoxicity. Reported as percent live cells compared to mock control.

Figure 7:
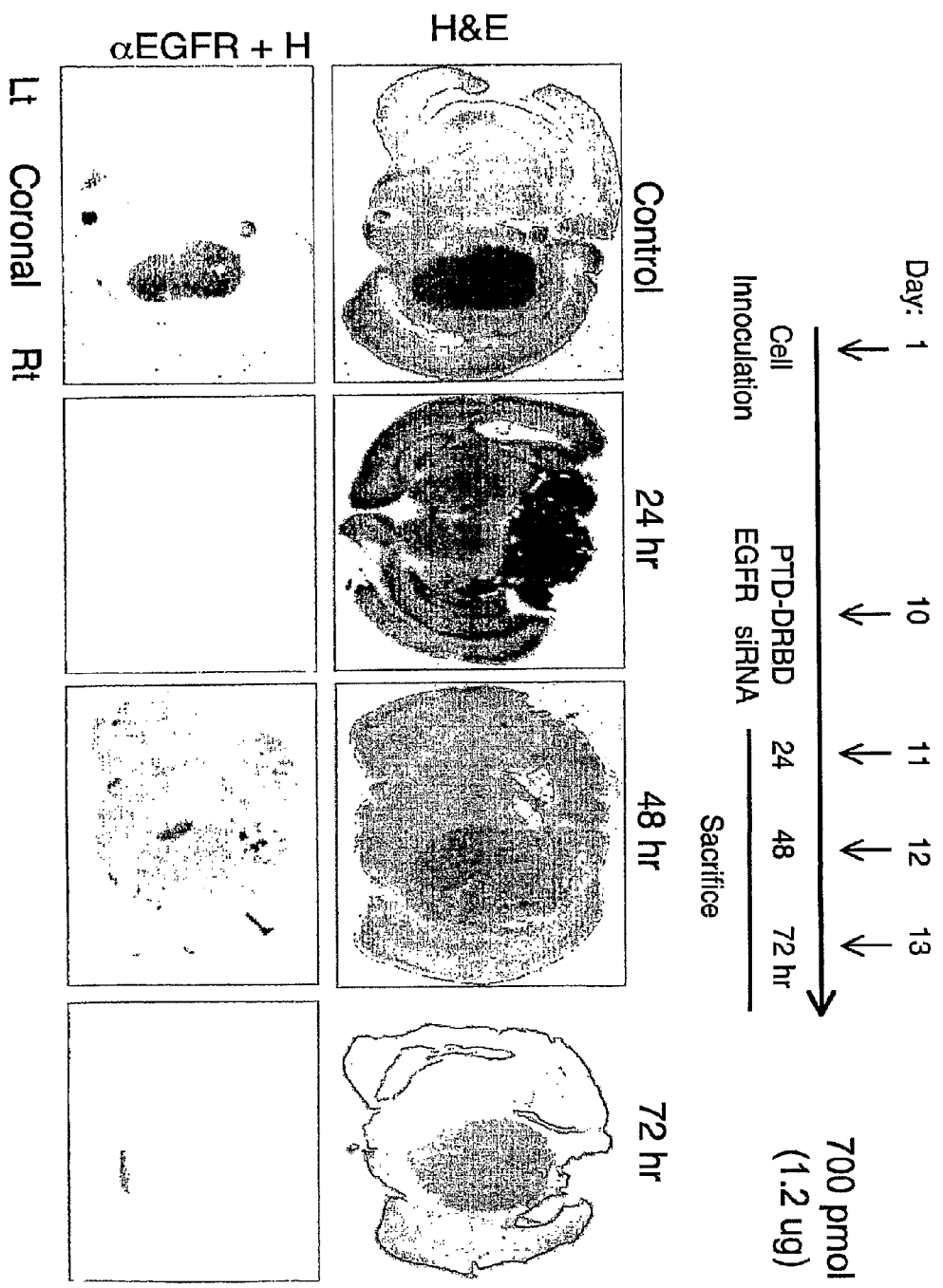

FIG. 7 shows nude mice were inoculated intracranially with 500,000 U87MG-EGFRvIII glioblastoma cells on day 1. On day 10, mice were treated with PTD-DRBD:siRNA targeting EGFRvIII. 24, 48, 72 hr post-addition of PTD-DRBD, mice were sacrificed and sequential coronal brain sections were obtained. Neighbor brain sections were either stained with H&E or IHC was performed using anti-EGFR antibodies plus H stain as indicated. Reduced EGFR staining at 24 hr followed by significant loss of EGFR staining at 48 and 72 hr is indicative of an EGFR RNAi response that ha spread throughout the glioblastoma.

DETAILED DESCRIPTION

As used herein and in the appended claims, the singular forms "a," "and," and "the" include plural referents unless the context clearly dictates otherwise. Thus, for example, reference to "a PTD" includes a plurality of such PTDs and reference to "the cell" includes reference to one or more cells known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

The ability to deliver functional agents to cells is problematical due to the bioavailability restriction imposed by the cell membrane. That is, the plasma membrane of the cell forms an effective barrier, which restricts the intracellular uptake of molecules to those which are sufficiently non-polar and smaller than approximately 500 daltons in size. Previous efforts to enhance the internalization of proteins have focused on fusing proteins with receptor ligands (Ng et al., Proc. Natl. Acad. Sci. USA, 99:10706-11, 2002) or by packaging them into caged liposomal carriers (Abu-Amer et al., J. Biol. Chem. 276:30499-503, 2001). However, these techniques often result in poor cellular uptake and intracellular sequestration into the endocytic pathway.

An advantage of the invention comprises intracellular delivery of nucleic acids which are otherwise difficult to transfect and where microinjection is not a possible option. For instance, primary lymphocytes are very difficult to transfect, requiring electroporation of DNA constructs. This process is very inefficient, killing 90-99% of the cells, and yielding therapeutic results in less than 10% of those which survive.

The disclosure provides fusion polypeptides and compositions useful in cellular transduction and cellular modulation. The fusion polypeptides of the disclosure comprise a transduction moiety domain comprising a membrane transport function and a nucleic acid binding domain sufficient to reversibly neutralize anionic charges on nucleic acids. In a further aspect, the fusion polypeptides of the invention comprise an anionic nucleic acid molecules (e.g., dsRNA) that is capable of interacting with the nucleic acid binding domain.

Using such methods and compositions, various diseases and disorders can be treated. For example, growth of tumor cells can be inhibited, suppressed, or destroyed upon delivery of an anti-tumor siRNA. For example, an anti-tumor siRNA can be an siRNA targeted to a gene encoding a polypeptide that promotes angiogenesis. Various angiogenic proteins associated with tumor growth are known in the art.

Thus, it is to be understood that the disclosure is not to be limited to any particular nucleic acid binding domain or nucleic acid domain. Rather, the nucleic acid domain can be any nucleic acid binding domain capable of reversibly neutralizing or reducing the anionic charge of a nucleic acid binding domain to be delivered. Furthermore, any anionically charged nucleic acid (e.g., dsRNA, siRNA and the like) can be delivered using the methods and compositions described herein.

The invention provides methods and compositions useful for delivery of interfering RNA agents. RNA interference (RNAi) is the process whereby messenger RNA (mRNA) is degraded by small interfering RNA (siRNA) derived from double-stranded RNA (dsRNA) containing an identical or very similar nucleotide sequence to that of a target gene to be silenced. This process prevents the production of a protein encoded by the targeted gene through post-transcriptional, pre-translational manipulation. Accordingly, silencing of dominant disease genes can be accomplished.

Genetic and biochemical studies involving plants and flies as well as worms have uncovered similar processes in which the dsRNA is cleaved into short interfering RNAs (siRNAs) by an enzyme called Dicer, a dsRNA endoribonuclease, (Bernstein et al., 2001; Hamilton & Baulcombe, 1999, Science 286: 950; Meister and Tuschl, 2004, Nature 431, 343-9), thus producing multiple molecules from the original single dsRNA. siRNAs are loaded into the multimeric RNAi Silencing Complex (RISC) resulting in both catalytic activation and mRNA target specificity (Hannon and Rossi, Nature 431, 371-378, 2004; Novina and Sharp, Nature 430, 161-164, 2004). During siRNA loading into RISC, the antisense or guide strand is separated from the siRNA and remains docked in Argonaute-2 (Ago2), the RISC catalytic subunit (Leuschner et al., EMBO Rep. 7, 314-320, 2006). mRNAs exported from the nucleus into the cytoplasm are thought to pass through activated RISCs prior to ribosomal arrival, thereby allowing for directed, post-transcriptional, pre-translational regulation of gene expression. In theory, each and every cellular mRNA can be regulated by induction of a selective RNAi response.

The ability of 21-23 bp siRNAs to efficiently induce an RNAi response in mammalian cells is now routine (Sontheimer, Nat. Rev. Mol. Cell. Biol. 6, 127-138, 2005). The 50% Inhibitory Concentration ($IC_{50}$) for siRNAs is in the 10-100 nM range, significantly below the best drugs with $IC_{50}$s in the 1-10 nM range. Consequently, due to its exquisite selectivity, RNAi has become a corner-stone for directed manipulation of cellular phenotypes, mapping genetic pathways, discovering and validating therapeutic targets, and has significant therapeutic potential.

The most interesting aspects of RNAi include (1) dsRNA, rather than single-stranded antisense RNA, is the interfering agent; (2) the process is highly specific and is remarkably potent (only a few dsRNA molecules per cell are required for effective interference); (3) the interfering activity (and presumably the dsRNA) can cause interference in cells and tissues far removed from the site of introduction. However, effective delivery of dsRNA is difficult. For example, a 21 bp dsRNA with a molecular weight of 13,860 Daltons cannot traverse the cell membrane to enter the cytoplasm, due to (1) the size and (2) the extremely negative (acidic) charge of the RNA.

Macromolecule fusion of cargo to a cationic Peptide Transduction Domain (PTD) (also termed Cell Penetrating peptide, CPP), such as TAT, 8×Arg, Antp (Snyder and Dowdy, 2005, Expert Opin. Drug Deliv. 2, 43-51) can be used to facilitate uptake of the macromolecule. PTDs can be used to deliver a wide variety of macromolecular cargo, including peptides, proteins, PNAs, and DNA vectors, into 100% of primary and transformed cells, into most, if not all, tissues. Pre-clinical models comprising PTD's and are currently being tested in several clinical trials (Schwarze et al., 1999, Science 285, 1569-1572; Eguchi et al., 2001, J. Biol. Chem. 276, 2620426210; Koppelhus et al., 2002, Antisense Nucleic Acid Drug Dev. 12, 51-63). Cationic PTDs enter cells by macropinocytosis, a specialized form of fluid phase uptake that all cells perform.

Biophysical studies on model vesicles suggests that cargo escape, from macropinosome vesicles into the cytoplasm, requires a pH decrease (Magzoub et al., 2005, Biochemistry 44, 14890-14897). The cationic charge of the PTDs or CPPs is essential for the molecules to traverse the cell membrane. Not surprisingly, conjugation of cationic PTDs (6-8 positive charges) to anionic siRNAs (~40 negative charges) results in charge neutralization and inactivation of the PTD with no siRNA entering the cells (Turner et al., 2007, Blood Cells Mol. Dis., 38(1), 1-7). However, chemical conjugation of cationic TAT to anionic RNA (or DNA) through a reversible disulfide bond results in charge neutralization of the cationic TAT PTD, thus eliminating or reducing the charge necessary to effectively traverse the cell surface and transduce the cell. In addition, due to a vast excess of negative charges on, for example, a 21 bp dsRNA versus the limited number of cationic charges on TAT, any free TAT PTD conjugated to the RNA results in aggregation and precipitation of the peptide-nucleic acid conjugate. Thus, while PTDs offer great potential to deliver macromolecular siRNAs into cells, PTD charge neutralization by the siRNA remains a formidable barrier for utilization of this approach.

The methods and compositions of the invention reversibly mask or neutralize the charge on a nucleic acid (e.g., dsRNA). The invention utilizes nucleic acid binding proteins to mask the anionic charge of the nucleic acid while maintaining a cationic charge necessary for traversal of the cellular membrane, thus permitting the cationic activity of the PTD to traverse the cell membrane and transduce a cell.

The invention provide methods and compositions useful to solve the macromolecular delivery problem. To circumvent PTD charge neutralization and solve the siRNA delivery problem, one embodiment of the invention provides a universal siRNA delivery approach comprising a PTD delivery domain operably linked to a dsRNA Binding Domain (DRBD) to form a PTD-DRBD construct that binds the siRNA and masks its negative charge.

DRBDs bind to siRNAs in a sequence-independent manner that allows for PTD-DRBD mediated delivery of siRNAs into cells. Using PTD-DRBD delivery of siRNAs, RNAi responses to multiple cellular targets were observed in all cell-types tested in a non-cytotoxic fashion, including primary fibroblasts, keratinocytes, T and B cells, macrophage, neuronal cells and human embryonic stem cells (hESCs).

For example, the invention demonstrates that a fusion protein of a PTD (e.g., TAT delivery peptide) and a dsRNA binding Domains (DRBDs) of PKR can effectively transduce cells. DRBDs bind to dsRNA and cover or mask dsRNA. In one aspect, one or more DBRDs can be used to cover the anionic surface of a dsRNA. For example, in one aspect, two to four DBRDs cover the surface of the dsRNA cylinder. DRBDs bind to dsRNA in a sequence independent fashion, which means that any nucleic acid (e.g., siRNA) can be delivered by this approach, regardless of sequence composition.

Alternative approaches could include engineering a disulfide bond or ester linkage between a nucleic acid (e.g., an siRNA) and a PTD-DRBD (e.g., TAT-DRBD) fusion protein to further increase the binding avidity. The complex is subsequently reduced and released inside the cell. Likewise an siRNA could be coated with DRBDs and a TAT conjugated directly to an siRNA in a biologically sensitive reversible manner.

Once the PTD-DRBD-nucleic acid complex traverses a cell's membrane, the PTD-DRBD-nucleic acid complex is subsequently reduced and released inside the cell. The dsRNA is then hydrolyzed by Dicer, an RNAse III-like ribonuclease, thereby releasing siRNA that silences a target gene.

Thus, the potential of RNAi to selectively treat human disease can more effectively be delivered to subjects and cells. The invention overcomes size and charge limitations making RNAi difficult to deliver or undeliverable. By reversibly neutralizing the anionic charge on a nucleic acid (e.g., dsRNA), the PTD can deliver anionically charged nucleic acids into the cell in vitro and in vivo.

A number of protein transduction domains/peptides are known in the art and have been demonstrated to facilitate uptake of heterologous molecules linked to the domain (e.g., cargo molecules). Such transduction domains facilitate uptake through a process referred to a macropinocytosis. However, macropinocytosis is a nonselective form of endocytosis that all cells perform. Consequently, this non-selective aspect of protein transduction also results in the majority of the PTD-cargo being transduced into non-target cells in vivo and thereby requires vastly more material. Therefore, pharmacologically speaking, PTDs resemble currently used small molecule therapeutics in their lack of specific delivery to the cells and tissues for which they are intended in vivo.

The discovery of several proteins which could efficiently pass through the plasma membrane of eukaryotic cells has led to the identification of a class of proteins from which peptide transduction domains have been derived. The best characterized of these proteins are the *Drosophila* homeoprotein antennapedia transcription protein (AntHD) (Joliot et al., New Biol. 3:1121-34, 1991; Joliot et al., Proc. Natl. Acad. Sci. USA, 88:1864-8, 1991; Le Roux et al., Proc. Natl. Acad. Sci. USA, 90:9120-4, 1993), the herpes simplex virus structural protein VP22 (Elliott and O'Hare, Cell 88:223-33, 1997), the HIV-1 transcriptional activator TAT protein (Green and Loewenstein, *Cell* 55:1179-1188, 1988; Frankel and Pabo, *Cell* 55:1189-1193, 1988), and more recently the cationic N-terminal domain of prion proteins. Not only can these proteins pass through the plasma membrane but the attachment of other proteins, such as the enzyme β-galactosidase, was sufficient to stimulate the cellular uptake of these complexes. Such chimeric proteins are present in a biologically active form within the cytoplasm and nucleus. Characterization of this process has shown that the uptake of these fusion polypeptides is rapid, often occurring within minutes, in a receptor independent fashion. Moreover, the transduction of these proteins does not appear to be affected by cell type and can efficiently transduce ~100% of cells in culture with no apparent toxicity (Nagahara et al., Nat. Med. 4:1449-52, 1998). In addition to full-length proteins, protein transduction domains have also been used successfully to induce the intracellular uptake of DNA (Abu-Amer, supra), antisense oligonucleotides (Astriab-Fisher et al., Pharm. Res, 19:744-54, 2002), small molecules (Polyakov et al., Bioconjug. Chem. 11:762-71, 2000) and even inorganic 40 nanometer iron particles (Dodd et al., J. Immunol. Methods 256:89-105, 2001; Wunderbaldinger et al., Bioconjug. Chem. 13:264-8, 2002; Lewin et al., Nat. Biotechnol. 18:410-4, 2000; Josephson et al., Bioconjug., Chem. 10:186-91, 1999) suggesting that there is no apparent size restriction to this process.

The fusion of a protein transduction domain (PTD) with a heterologous molecule (e.g., a polynucleotide, small molecule, or protein) is sufficient to cause their transduction into a variety of different cells in a concentration-dependent manner. Moreover, this technique for protein delivery appears to circumvent many problems associated with DNA and drug based techniques. However, it is important to note that RNAi molecules are highly anionic and that such nucleic acid molecules have not been effectively transduced using PTDs prior to this invention.

PTDs are typically cationic in nature. These cationic protein transduction domains track into lipid raft endosomes carrying with them their linked cargo and release their cargo into the cytoplasm by disruption of the endosomal vesicle. Examples of PTDs include AntHD, TAT, VP22, cationic prion protein domains and functional fragments thereof. The disclosure provides methods and compositions that combine the use of PTDs such as TAT and poly-Arg, with a nucleic acid binding domain capable of neutralizing the anionic charge on a nucleic acid (i.e., the "cargo") domain. These compositions provide methods whereby a therapeutic or diagnostic agent can be targeted to cells whereby the PTD causes uptake of the composition into the targeted cells.

In general, the transduction domain of the fusion molecule can be nearly any synthetic or naturally-occurring amino acid sequence that can transduce or assist in the transduction of the fusion molecule. For example, transduction can be achieved in accordance with the invention by use of a protein transduction domain, such as an HIV TAT protein or fragment thereof, that is covalently linked at the N-terminal or C-terminal end to either a nucleic acid binding domain (e.g., a DRBD), a nucleic acid coated with a nucleic acid binding domain (e.g., a DRBD) or both. Alternatively, the protein transduction domain can comprise the Antennapedia homeodomain or the HSV VP22 sequence, the N-terminal fragment of a prion protein or suitable transducing fragments thereof such as those known in the art.

The type and size of the PTD will be guided by several parameters including the extent of transduction desired. Typically the PTD will be capable of transducing at least about 20%, 25%, 50%, 75%, 80% or 90%, 95%, 98% and up to, and including, about 100% of the cells. Transduction efficiency, typically expressed as the percentage of transduced cells, can be determined by several conventional methods.

PTDs will manifest cell entry and exit rates (sometimes referred to as $k_1$ and $k_2$, respectively) that favor at least picomolar amounts of the fusion molecule in the cell. The entry and exit rates of the PTD and any cargo can be readily determined or at least approximated by standard kinetic analysis using detectably-labeled fusion molecules. Typically, the ratio of the entry rate to the exit rate will be in the range of between about 5 to about 100 up to about 1000.

In one aspect, a PTD useful in the methods and compositions of the invention comprise a peptide featuring substantial alpha-helicity. It has been discovered that transduction is optimized when the PTD exhibits significant alpha-helicity. In another embodiment, the PTD comprises a sequence containing basic amino acid residues that are substantially aligned along at least one face of the peptide. A PTD domain of the useful in the invention may be a naturally occurring peptide or a synthetic peptide.

In another aspect of the invention, the PTD comprises an amino acid sequences comprising a strong alpha helical structure with arginine (Arg) residues down the helical cylinder.

In yet another embodiment, the PTD domain comprises a peptide represented by the following general formula: $B_1$-$X_1$-$X_2$-$X_3$-$B_2$-$X_4$-$X_5$-$B_3$ (SEQ ID NO:1) wherein $B_1$, $B_2$, and $B_3$ are each independently a basic amino acid, the same or different; and $X_1$, $X_2$, $X_3$, $X_4$ and $X_5$ are each independently an alpha-helix enhancing amino acid, the same or different.

In another embodiment, the PTD domain is represented by the following general formula: $B_1$-$X_1$-$X_2$-$B_2$-$B_3$-$X_3$-$X_4$-$B_4$ (SEQ ID NO:2) wherein $B_1$, $B_2$, $B_3$, and $B_4$ are each independently a basic amino acid, the same or different; and $X_1$, $X_2$, $X_3$, and $X_4$ are each independently an alpha-helix enhancing amino acid the same or different.

Additionally, PTD domains comprise basic residues, e.g., lysine (Lys) or arginine (Arg), and further can include at least one proline (Pro) residue sufficient to introduce "kinks" into the domain. Examples of such domains include the transduction domains of prions. For example, such a peptide comprises KKRPKPG (SEQ ID NO:3).

In one embodiment, the domain is a peptide represented by the following sequence: X-X-R-X-(P/X)-(B/X)-B-(P/X)-X-B-(B/X) (SEQ ID NO:4), wherein X is any alpha helical promoting residue such as alanine; P/X is either proline or X as previously defined; B is a basic amino acid residue, e.g., arginine (Arg) or lysine (Lys); R is arginine (Arg) and B/X is either B or X as defined above.

In another embodiment the PTD is cationic and consists of between 7 and 10 amino acids and has the formula $KX_1RX_2X_1$ (SEQ ID NO:5) wherein $X_1$ is R or K and $X_2$ is any amino acid. An example of such a peptide comprises RKKRRQRRR (SEQ ID NO:6).

Additional transducing domains in accord with this invention include a TAT fragment that comprises at least amino acids 49 to 56 of TAT up to about the full-length TAT sequence (see, e.g., SEQ ID NO:7). A TAT fragment may include one or more amino acid changes sufficient to increase the alpha-helicity of the fragment. In some instances, the amino acid changes introduced will involve adding a recognized alpha-helix enhancing amino acid. Alternatively, the amino acid changes will involve removing one or more amino acids from the TAT fragment the impede alpha helix formation or stability. In a more specific embodiment, the TAT fragment will include at least one amino acid substitution with an alpha-helix enhancing amino acid. Typically the TAT fragment will be made by standard peptide synthesis techniques although recombinant DNA approaches may be used in some cases. In one embodiment, the substitution is selected so that at least two basic amino acid residues in the TAT fragment are substantially aligned along at least one face of that TAT fragment. In a more specific embodiment, the substitution is chosen so that at least two basic amino acid residues in the TAT 49-56 sequence are substantially aligned along at least one face of that sequence.

Additional transduction proteins (PTDs) that can be used in the compositions and methods of the invention include the TAT fragment in which the TAT 49-56 sequence has been modified so that at least two basic amino acids in the sequence are substantially aligned along at least one face of the TAT fragment. Illustrative TAT fragments include at least one specified amino acid substitution in at least amino acids 49-56 of TAT which substitution aligns the basic amino acid residues of the 49-56 sequence along at least one face of the segment and typically the TAT 49-56 sequence.

Also included are chimeric PTD domains. Such chimeric transducing proteins include parts of at least two different transducing proteins. For example, chimeric transducing proteins can be formed by fusing two different TAT fragments, e.g., one from HIV-1 and the other from HIV-2 or one from a prion protein and one from HIV.

PTDs can be linked or fused with any number of nucleic acid binding domains (e.g., DRBDs). The nucleic acid binding domain serves to neutralize or reduce the anionic charge of a nucleic acid molecule to be delivered using PTDs. The nucleic acid binding domain promotes uptake of a fusion construct comprising a nucleic acid by sufficiently reducing the anionic charge such that the cationic charge of the PTD domain is sufficient to transduce a cell by traversing a cell's membrane.

Exemplary RNA binding proteins that can be linked to a PTD include histone, RDE-4 protein, or protamine. Protamines are arginine-rich proteins and include, for example, a sequence RSRRRRRRSCQTRRR (SEQ ID NO:15). Additional dsRNA binding proteins and their Accession numbers in parenthesis include: PKR (AAA36409, AAA61926, Q03963), TRBP (P97473, AAA36765), PACT (AAC25672, AAA49947, NP609646), Staufen (AAD17531, AAF98119, AAD17529, P25159), NFAR1 (AF167569), NFAR2 (AF167570, AAF31446, AAC71052, AAA19960, AAA19961, AAG22859), SPNR (AAK20832, AAF59924, A57284), RHA (CAA71668, AAC05725, AAF57297), NREBP (AAK07692, AAF23120, AAF54409, T33856), kanadaptin (AAK29177, AAB88191, AAF55582, NP499172, NP198700, BAB19354), HYLL (NP563850), hyponastic leaves (CAC05659, BAB00641), ADAR1 (AAB97118, P55266, AAK16102, AAB51687, AF051275), ADAR2 P78563, P51400, AAK17102, AAF63702), ADAR3 (AAF78094, AAB41862, AAF76894), TENR (XP059592, CAA59168), RNaseIII (AAF80558, AAF59169, Z81070Q02555/S55784, P05797), and Dicer (BAA78691, AF408-401, AAF56056, S44849, AAF03534, Q9884), RDE-4 (AY071926), FLJ20399 (NP060273, BAB26260), CG1434 (AAF48360, EAA12065, CAA21662), CG13139 (XP059208, XP143416, XP110450, AAF52926, EEA14824), DGCRK6 (BAB83032, XP110167) CG1800 (AAF57175, EAA08039), FLJ20036 (AAH22270, XP134159), MRP-L45 (BAB14234, XP129893), CG2109 (AAF52025), CG12493 (NP647927), CG10630 (AAF50777), CG17686 (AAD50502), T22A3.5 (CAB03384) and accession number EAA14308. The sequences of such nucleic acid binding proteins are known in the art based upon the accession numbers. The sequences associated with said accession numbers are specifically incorporated herein by reference in their entireties.

Nucleic acid binding polypeptides can comprise any of the full length polypeptides of the foregoing accession numbers, fragments of any of the foregoing as well as modified polypeptides comprising from 1-10 amino acid substitution comprising a sequence as set forth in the above-identified accession numbers.

It will be understood that the PTD may be fused to a nucleic acid wherein the nucleic acid is coated with one or more nucleic acid binding domains sufficient to reduce any anionic charge. Alternatively, the PTD may be operably linked to a nucleic acid binding domain (e.g., a DRBD) which in-turn coats an anionically charged nucleic acid.

A PTD and an anionic nucleic acid molecule (e.g., a dsRNA) can be linked using phosphoramidate, phosphorothioate, or phosphodiester linkers. For example, an siRNA comprising a 3'-amino group with a 3-carbon linker may be utilized for linking the siRNA to a PTD. The siRNA is conjugated to the PTD via a heterobifunctional cross linker.

A disulfide bond between the PTD and an siRNA or between the DRBD and the siRNA can be formed to facilitated targeted/time release. A disulfide bond between a PTD and nucleic acid or DRBD and a nucleic acid can be cleaved to release the nucleic acid.

Where the PTD is operably linked to a nucleic acid binding domain (e.g., a DRBD), the two domains can be linked by peptide linkers, chemical synthesized or expressed by a polynucleotide construct where the domains are operably linked such that their coding frames generate a single functional polypeptide comprising a PTD domain and a DRBD domain.

As noted, components of the fusion polypeptides disclosed herein, e.g., a PTD-nucleic acid binding domain (e.g., a DRBD), and a nucleic acid domain, and optionally peptide linkers, can be organized in nearly any fashion provided that the fusion polypeptide has the function for which it was intended (e.g., sufficiently cationically charged). The invention provides fusion polypeptides or chimeric proteins comprising one or more PTDs linked to one or more nucleic acid binding domain which is either directly or indirectly linked to a nucleic acid domain (e.g., a therapeutic or diagnostic DNA, RNA, siRNA and the like). Each of the several domains may be directly linked or may be separated by a linker peptide. The domains may be presented in any order. Additionally, the fusion polypeptides may include tags, e.g., to facilitate identification and/or purification of the fusion polypeptide, such as a 6×HIS tag.

Peptide linkers that can be used in the fusion polypeptides and methods of the invention will typically comprise up to about 20 or 30 amino acids, commonly up to about 10 or 15 amino acids, and still more often from about 1 to 5 amino acids. The linker sequence is generally flexible so as not to hold the fusion molecule in a single rigid conformation. The linker sequence can be used, e.g., to space the PTD domain from the nucleic acid binding domain and/or nucleic acid domain. For example, the peptide linker sequence can be positioned between the protein transduction domain and the nucleic acid domain, e.g., to provide molecular flexibility. The length of the linker moiety is chosen to optimize the biological activity of the polypeptide comprising a PTD domain fusion construct and can be determined empirically without undue experimentation. The linker moiety should be long enough and flexible enough to allow a nucleic acid binding domain to freely interact with a nucleic acid or vice versa. Examples of linker moieties are --Gly-Gly-, GGGGS (SEQ ID NO:8), (GGGGS)$_N$ (SEQ ID NO:9), GKSSGSG-SESKS (SEQ ID NO:10), GSTSGSGKSSEGKG (SEQ ID NO:11), GSTSGSGKSSEGSGSTKG (SEQ ID NO:12), GSTSGSGKPGSGEGSTKG (SEQ ID NO:13), or EGKSSGSGSESKEF (SEQ ID NO:14). Linking moieties are described, for example, in Huston et al., Proc. Nat'l Acad. Sci. 85:5879, 1988; Whitlow et al., Protein Engineering 6:989, 1993; and Newton et al., Biochemistry 35:545, 1996. Other suitable peptide linkers are those described in U.S. Pat. Nos. 4,751,180 and 4,935,233, which are hereby incorporated by reference.

The disclosure provides chimeric/fusion polypeptides comprising a PTD and a nucleic acid binding protein. In one aspect, the chimeric/fusion polypeptide comprises a PTD linked to a double stranded RNA binding protein that shields the anionic dsRNA charge.

In one aspect, the fusion construct of the invention may comprise, in addition to the PTD and nucleic acid binding domain, a targeting domain. The targeting domain can be a receptor or receptor ligand useful for directing the fusion construct to a particular cell type that expresses the cognate binding domain.

A polypeptide (including a fusion polypeptide) refers to a polymer in which the monomers are amino acid residues which are joined together through amide bonds. When the amino acids are alpha-amino acids, either the L-optical isomer or the D-optical isomer can be used. A polypeptide encompasses an amino acid sequence and includes modified sequences such as glycoproteins, retro-inverso polypeptides, D-amino acid modified polypeptides, and the like. A polypeptide includes naturally occurring proteins, as well as those which are recombinantly or synthetically synthesized. A polypeptide may comprise more than one domain have a function that can be attributed to the particular fragment or portion of a polypeptide. A domain, for example, includes a portion of a polypeptide which exhibits at least one useful epitope or functional domain. Two or more domains may be functionally linked such that each domain retains its function yet comprises a single polypeptide (e.g., a fusion polypeptide). For example, a functional fragment of a PTD includes a fragment which retains transduction activity. Biologically functional fragments, for example, can vary in size from a polypeptide fragment as small as an epitope capable of binding an antibody molecule, to a large polypeptide capable of participating in the characteristic induction or programming of phenotypic changes within a cell.

In some embodiments, retro-inverso peptides are used. "Retro-inverso" means an amino-carboxy inversion as well as enantiomeric change in one or more amino acids (i.e., levantory (L) to dextrorotary (D)). A polypeptide of the disclosure encompasses, for example, amino-carboxy inversions of the amino acid sequence, amino-carboxy inversions containing one or more D-amino acids, and non-inverted sequence containing one or more D-amino acids. Retro-inverso peptidomimetics that are stable and retain bioactivity can be devised as described by Brugidou et al. (Biochem. Biophys. Res. Comm. 214(2): 685-693, 1995) and Chorev et al. (Trends Biotechnol. 13(10): 438-445, 1995). The overall structural features of a retro-inverso polypeptide are similar to those of the parent L-polypeptide. The two molecules, however, are roughly mirror images because they share inherently chiral secondary structure elements. Main-chain peptidomimetics based on peptide-bond reversal and inversion of chirality represent important structural alterations for peptides and proteins, and are highly significant for biotechnology. Antigenicity and immunogenicity can be achieved by metabolically stable antigens such as all-D- and retro-inverso-isomers of natural antigenic peptides. Several PTD-derived peptidomimetics are provided herein.

Polypeptides and fragments can have the same or substantially the same amino acid sequence as the naturally derived polypeptide or domain. "Substantially identical" means that an amino acid sequence is largely, but not entirely, the same, but retains a functional activity of the sequence to which it is related. An example of a functional activity is that the fragment is capable of transduction, or capable of binding to an RNA. For example, fragments of full length TAT are described herein that have transduction activity. In general two polypeptides or domains are "substantially identical" if their sequences are at least 85%, 90%, 95%, 98% or 99% identical, or if there are conservative variations in the sequence. A computer program, such as the BLAST program (Altschul et al., 1990) can be used to compare sequence identity.

A polypeptide of the disclosure can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a peptide or polypeptide, including the peptide backbone, the amino acid side-chains and the amino or carboxyl termini. It will be appreciated that the same type of modification may be present in the same or varying degrees at several sites in a given peptide or polypeptide. Also, a given peptide or polypeptide may contain many types of modifications. A peptide or polypeptide may be branched, for example, as a result of ubiquitination, and they may be cyclic, with or without branching. Cyclic, branched, and branched cyclic peptides and polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann N.Y. Acad Sci 663:48-62 (1992).)

A polypeptide domain or a fusion polypeptide of the disclosure can be synthesized by commonly used methods such as those that include t-BOC or FMOC protection of alpha-amino groups. Both methods involve stepwise synthesis in which a single amino acid is added at each step starting from the C terminus of the peptide (See, Coligan, et al., Current Protocols in Immunology, Wiley Interscience, 1991, Unit 9). Polypeptides of the disclosure can also be synthesized by the well known solid phase peptide synthesis methods such as those described by Merrifield, J. Am. Chem. Soc., 85:2149, 1962; and Stewart and Young, Solid Phase Peptides Synthesis, Freeman, San Francisco, 1969, pp. 27-62, using a copoly (styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with a 1% acetic acid solution, which is then lyophilized to yield the crude material. The peptides can be purified by such techniques as gel filtration on Sephadex G-15 using 5% acetic acid as a solvent. Lyophilization of appropriate fractions of the column eluate yield homogeneous peptide, which can then be characterized by standard techniques such as amino acid analysis, thin layer chromatography, high performance liquid chromatography, ultraviolet absorption spectroscopy, molar rotation, or measuring solubility. If desired, the peptides can be quantitated by the solid phase Edman degradation.

In another aspect, the disclosure provides a method of producing a fusion polypeptide comprising a PTD domain and a nucleic acid binding domain or RNA by growing a host cell comprising a polynucleotide encoding the fusion polypeptide under conditions that allow expression of the polynucleotide, and recovering the fusion polypeptide. A polynucleotide encoding a fusion polypeptide of the disclosure can be operably linked to a promoter for expression in a prokaryotic or eukaryotic expression system. For example, such a polynucleotide can be incorporated in an expression vector. Recombinant molecular biology techniques can be used to link, for example, a PTD domain and a DRBD domain to generate a polynucleotide of the disclosure such that upon expression the polypeptide comprising the domains are functionally operative.

The term "operably linked" or "operably associated" refers to functional linkage between regulatory and/or coding domains of a polynucleotide regulated by the regulatory sequence as well as the link between encoded domains of the fusion polypeptides such that each domain is linked in-frame to give rise to the desired polypeptide sequence.

Accordingly, the disclosure also includes isolated polynucleotides (e.g., DNA, cDNA, or RNA) encoding the polypeptides, including fusion polypeptides, of the disclosure. Included are polynucleotides that encode analogs, mutants, conservative variations, and variants of the polypeptides described herein. The term "isolated" as used herein refers to a polynucleotide that is substantially free of proteins, lipids, and other polynucleotides with which an in vivo-produced polynucleotide naturally associates. Typically, the polynucleotide is at least 70%, 80%, or 90% isolated from other matter, and conventional methods for synthesizing polynucleotides in vitro can be used in lieu of in vivo methods. As used herein, "polynucleotide" refers to a polymer of deoxyribonucleotides or ribonucleotides, in the form of a separate fragment or as a component of a larger genetic construct (e.g., by operably linking a promoter to a polynucleotide encoding a peptide of the disclosure or operably linking heterologous coding domains). Numerous genetic constructs (e.g., plasmids and other expression vectors) are known in the art and can be used to produce the polypeptides of the disclosure in cell-free systems or prokaryotic or eukaryotic (e.g., yeast, insect, or mammalian) cells. By taking into account the degeneracy of the genetic code, one of ordinary skill in the art can readily synthesize polynucleotides encoding the polypeptides of the disclosure. The polynucleotides of the disclosure can readily be used in conventional molecular biology methods to produce the peptides of the disclosure.

Such polynucleotides include naturally occurring, synthetic, and intentionally manipulated polynucleotides. A polynucleotide encoding a PTD domain or a DRBD domain or functional fragments thereof includes sequences that are degenerate as a result of the genetic code. Polynucleotide sequences that encode a PTD or DRBD or functional fragment thereof can be readily ascertained based upon the polypeptide sequences provided herein and with reference to the accession numbers provided herein. There are 20 natural amino acids, most of which are specified by more than one codon. Therefore, polynucleotides comprising all degenerate nucleotide sequences are included so long as the resulting polypeptide comprises an amino acid resulting a function PTD or DRBD polypeptide domain.

Polynucleotides encoding a fusion polypeptide or domains thereof can be inserted into an "expression vector." The term "expression vector" refers to a genetic construct such as a plasmid, virus or other vehicle known in the art that can be engineered to contain a polynucleotide encoding a polypeptide of the disclosure. Such expression vectors are typically plasmids that contain a promoter sequence that facilitates transcription of the inserted genetic sequence in a host cell. The expression vector typically contains an origin of replication, and a promoter, as well as genes that allow phenotypic selection of the transformed cells (e.g., an antibiotic resistance gene). Various promoters, including inducible and constitutive promoters, can be utilized in the disclosure. Typically, the expression vector contains a replicon site and control sequences that are derived from a species compatible with the host cell.

Transformation or transfection of a host cell with a polynucleotide can be carried out using conventional techniques well known to those skilled in the art. For example, where the host cell is $E. coli$, competent cells that are capable of DNA uptake can be prepared using the $CaCl_2$, $MgCl_2$ or $RbCl$ methods known in the art. Alternatively, physical means, such as electroporation or microinjection can be used. Electroporation allows transfer of a polynucleotide into a cell by high voltage electric impulse. Additionally, polynucleotides can be introduced into host cells by protoplast fusion, using methods well known in the art. Suitable methods for transforming eukaryotic cells, such as electroporation and lipofection, also are known.

"Host cells" encompassed by of the disclosure are any cells in which the polynucleotides of the disclosure can be used to express the fusion polypeptide or functional domains thereof. The term also includes any progeny of a host cell. Host cells, which are useful, include bacterial cells, fungal cells (e.g., yeast cells), plant cells and animal cells. A fusion polypeptide of the disclosure can be produced by expression of polynucleotide encoding a fusion polypeptide in prokaryotes. These include, but are not limited to, microorganisms, such as bacteria transformed with recombinant bacteriophage DNA, plasmid DNA, or cosmid DNA expression vectors encoding a fusion polypeptide of the disclosure. The constructs can be expressed in $E. coli$ in large scale for in vitro assays. Host cells can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology (1986)). As representative examples of appropriate hosts, there may be mentioned: fungal cells, such as yeast; insect cells such as *Drosophila* S2 and *Spodoptera* Sf9; animal cells such as CHO, COS or Bowes melanoma; plant cells, and the like. The selection of an appropriate host is deemed to be within the scope of those skilled in the art from the teachings herein.

Host cells can be eukaryotic host cells (e.g., mammalian cells). In one aspect, the host cells are mammalian production cells adapted to grow in cell culture. Examples of such cells commonly used in the industry are CHO, VERO, BHK, HeLa, CV1 (including Cos; Cos-7), MDCK, 293, 3T3, C127, myeloma cell lines (especially murine), PC12 and W138 cells. Chinese hamster ovary (CHO) cells are widely used for the production of several complex recombinant proteins, e.g. cytokines, clotting factors, and antibodies (Brasel et al., Blood 88:2004-2012, 1996; Kaufman et al., J. Biol Chem 263: 6352-6362, 1988; McKinnon et al., J Mol Endocrinol 6:231-239, 1991; Wood et al., J. Immunol. 145:3011-3016, 1990). The dihydrofolate reductase (DHFR)-deficient mutant cell lines (Urlaub et al., Proc Natl Acad Sci USA 77:4216-4220, 1980) are the CHO host cell lines commonly used because the efficient DHFR selectable and amplifiable gene expression system allows high level recombinant protein expression in these cells (Kaufman, Meth Enzymol 185:527-566, 1990). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

Eukaryotic systems, and typically mammalian expression systems, allow for proper post-translational modifications of expressed mammalian proteins to occur. Eukaryotic cells that possess the cellular machinery for proper processing of the primary transcript, glycosylation, phosphorylation, and advantageously secretion of the gene product can be used as host cells for the expression of the PTD-fusion polypeptide of the disclosure. Such host cell lines may include, but are not limited to, CHO, VERO, BHK, HeLa, COS, MDCK, Jurkat, HEK-293, and WI38.

For long-term, high-yield production of recombinant proteins, stable expression is typically used. Rather than using expression vectors that contain viral origins of replication, host cells can be transformed with the cDNA encoding a fusion polypeptide of the disclosure controlled by appropriate expression control elements (e.g., promoter, enhancer, sequences, transcription terminators, polyadenylation sites, and the like), and a selectable marker. The selectable marker confers resistance to a selective killing agent and upon stable integration of the heterologous polynucleotide, allows growth of resistant cells. Such resistant cells grow to form foci that, in turn, can be cloned and expanded into cell lines. For example, following the introduction of foreign DNA, engineered cells may be allowed to grow for 1-2 days in an enriched media, and then are switched to a selective media. A number of selection systems may be used, including, but not limited to, the herpes simplex virus thymidine kinase (Wigler et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy et al., Cell, 22:817, 1980) genes can be employed in tk-, hgprt- or aprt-cells, respectively. Also, antimetabolite resistance can be used as the basis of selection for dhfr, which confers resistance to methotrexate (Wigler et al., Proc. Natl. Acad. Sci. USA, 77:3567, 1980; O'Hare et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin et al., J. Mol. Biol., 150:1, 1981); and hygro, which confers resistance to hygromycin genes (Santerre et al., Gene, 30:147, 1984). Additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:8047, 1988); and ODC (ornithine decarboxylase), which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

In yeast, a number of vectors containing constitutive or inducible promoters may be used (see, e.g., Current Protocols in Molecular Biology, Vol. 2, Ed. Ausubel et al., Greene Publish. Assoc. & Wiley Interscience, Ch. 13, 1988; Grant et al., "Expression and Secretion Vectors for Yeast," in Methods in Enzymology, Eds. Wu & Grossman, Acad. Press, N.Y., Vol. 153, pp. 516-544, 1987; Glover, DNA Cloning, Vol. II, IRL Press, Wash., D.C., Ch. 3, 1986; "Bitter, Heterologous Gene Expression in Yeast," Methods in Enzymology, Eds. Berger & Kimmel, Acad. Press, N.Y., Vol. 152, pp. 673-684, 1987; and The Molecular Biology of the Yeast *Saccharomyces*, Eds. Strathern et al., Cold Spring Harbor Press, Vols. I and II, 1982). A constitutive yeast promoter, such as ADH or LEU2, or an inducible promoter, such as GAL, may be used ("Cloning in Yeast," Ch. 3, R. Rothstein In: DNA Cloning Vol. 11, A Practical Approach, Ed. D M Glover, IRL Press, Wash., D.C., 1986). Alternatively, vectors may be used which promote integration of foreign DNA sequences into the yeast chromosome.

In one aspect of the disclosure, distinct domains (e.g., a PTD or DRBD) are expressed from a host cell comprising a polynucleotide encoding the domain. The domain is then purified using art-known methods (as described further herein). The domains are then chemically linked directly or indirectly (e.g., with a peptide linker) to form a fusion polypeptide. Alternatively, a polynucleotide encoding a fusion polypeptide is expressed in a host cell and the fusion polypeptide is purified using art known methods. Regardless of the method by which the fusion polypeptide is formed; the fusion polypeptide is then contacted with a nucleic acid (e.g., an anionically charged dsRNA) under conditions whereby the nucleic acid binding protein (e.g., DRBD) interacts with the nucleic acid in a sequence independent manner. The fusion construct may comprise one or more nucleic acid binding proteins (e.g., DRBD). In one aspect, the nucleic acid molecules (e.g., the dsRNA) interacts with at least two nucleic acid binding proteins.

Any of various art-known methods for protein purification can be used to isolate a polypeptide domain or fusion polypeptide of the disclosure. For example, preparative chromatographic separations and immunological separations (such as those employing monoclonal or polyclonal antibodies) can be used. Carrier peptides can facilitate isolation of fusion polypeptides. Such carrier peptides or purification tags can be operably linked to a PTD, DRBD or PTD-DRBD fusion polypeptide of the disclosure. For example, glutathione-S-transferase (GST) allows purification with a glutathione agarose affinity column. When either Protein A or the ZZ domain from *Staphylococcus aureus* is used as the tag, purification can be accomplished in a single step using an IgG-sepharose affinity column. The pOprF-peptide, which is the N-terminal half of the *P. aeruginosa* outer membrane protein F, can readily be purified because it is the prominent protein species in outer membrane preparations. If desired, the fusion peptides can be purified using reagents that are specifically reactive with (e.g., specifically bind) the cathelicidin functional fragment of the fusion peptide. For example, monoclonal or polyclonal antibodies that specifically bind the DRBD or PTD domain can be used in conventional purification methods. Techniques for producing such antibodies are well known in the art. A fusion polypeptide of the disclosure can also be engineered to contain a cleavage site to aid in protein recovery or other linker moiety separating a PTD from a nucleic acid binding protein or dsRNA molecule.

As used herein, a nucleic acid domain can be any polynucleotide (e.g., a ribozyme, antisense molecule, polynucleotide, oligonucleotide and the like). In the specific examples provided herein, the nucleic acid domain comprises a dsRNA.

dsRNA comprising siRNA sequences that are complementary to a nucleotide sequence of the target gene can be prepared in any number of methods. Methods and techniques for identifying siRNA sequences are known in the art. The siRNA nucleotide sequence can be obtained from the siRNA Selection Program, Whitehead Institute for Biomedical Research, Massachusetts Institute of Technology, Cambridge, Mass. (currently available at hypertext transfer protocol: //jura.wi.mit.edu/bioc/siRNAext/) after supplying the Accession Number or GI number from the National Center for Biotechnology Information website (available on the World Wide Web at ncbi.nlm.nih.gov). Alternatively, dsRNA containing appropriate siRNA sequences can be ascertained using the strategy of Miyagishi and Taira (2003). Typically, the longer the dsRNA sequence the increase in anionic charge requiring additional DRBDs or other nucleic acid binding proteins. Commercially available RNAi designer algorithms also exist (hypertext transfer protocol: //rnaidesigner.invitrogen.com/rnaiexpress/). Preparation of RNA to order is commercially available. Once obtained the RNA molecule comprising the siRNA sequence can be bound by a nucleic acid binding protein or directly linked or indirectly linked to a PTD domain of the disclosure.

The dsRNA is operably linked to a PTD or is incubated under conditions such that a PTD comprising a nucleic acid binding protein (e.g., a DRBD) or a nucleic acid binding protein interacts with the dsRNA. Typically the interaction of the dsRNA with the nucleic acid binding protein results in a reduction of the overall anionic charge of the complex (e.g., the DRBD and dsRNA).

The methods, compositions, and fusion polypeptides of the invention provide enhanced uptake and release of nucleic acid molecules.

The term "therapeutic" is used in a generic sense and includes treating agents, prophylactic agents, and replacement agents. Examples of therapeutic molecules include, but are not limited to, cell cycle control agents; agents which inhibit cyclin protein production, such as siRNA polynucleotides to the cyclin G1 and cyclin D1 genes; dsRNA that can be cleaved to provide siRNA molecules directed to specific growth factors such as, for example, epidermal growth factor (EGF), vascular endothelial growth factor (VEGF), erythropoietin, G-CSF, GM-CSF, TGF-α, TGF-β, and fibroblast growth factor; cytokines, including, but not limited to, Interleukins 1 through 13 and tumor necrosis factors; anticoagulants, anti-platelet agents; TNF receptor domains and the like.

Using such methods and compositions, various diseases and disorders can be treated. For example, growth of tumor cells can be inhibited, suppressed, or destroyed upon delivery of an anti-tumor siRNA. For example, an anti-tumor siRNA can be an siRNA targeted to a gene encoding a polypeptide that promotes angiogenesis. Various angiogenic proteins associated with tumor growth are known in the art.

The fusion polypeptides of the invention are useful for the delivery of anionically charged nucleic acid molecules (e.g., dsRNA, siRNA, DNA, antisense, ribozymes and the like) for the treatment and/or diagnosis of a number of diseases and disorders. For example, the fusion polypeptides can be used in the treatment of cell proliferative disorders, wherein the nucleic acid binding domain (e.g., DRBD) neutralizes that charge on nucleic acids used to target genes that induce cell proliferation. The PTD domain facilitates uptake of the fusion polypeptide and the nucleic acid binding domain (e.g., DRBD). Thus, the fusion polypeptide is useful for treatment of cells having cell proliferative disorders. Similarly, the fusion polypeptides of the invention can be used to treatment inflammatory diseases and disorders, infections, vascular disease and disorders and the like.

Thus, it is to be understood that the disclosure is not to be limited to any particular nucleic acid binding domain or nucleic acid domain. Rather, the nucleic acid domain can be any nucleic acid binding domain capable of neutralizing or reducing the anionic charge of a nucleic acid to be delivered. Furthermore, any anionically charged nucleic acid (e.g., dsRNA, siRNA and the like) can be delivered using the methods of the invention.

Typically a fusion polypeptide of the disclosure will be formulated with a pharmaceutically acceptable carrier, although the fusion polypeptide may be administered alone, as a pharmaceutical composition.

A pharmaceutical composition according to the disclosure can be prepared to include a fusion polypeptide of the disclosure, into a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The pharmaceutical compositions according to the disclosure may be administered locally or systemically. By "therapeutically effective dose" is meant the quantity of a fusion polypeptide according to the disclosure necessary to prevent, to cure, or at least partially arrest the symptoms of a disease or disorder (e.g., to inhibit cellular proliferation). Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249: 1527, (1990); Gilman et al. (eds.) (1990), each of which is herein incorporated by reference.

As used herein, "administering a therapeutically effective amount" is intended to include methods of giving or applying a pharmaceutical composition of the disclosure to a subject that allow the composition to perform its intended therapeutic function. The therapeutically effective amounts will vary according to factors, such as the degree of infection in a subject, the age, sex, and weight of the individual. Dosage regima can be adjusted to provide the optimum therapeutic response. For example, several divided doses can be administered daily or the dose can be proportionally reduced as indicated by the exigencies of the therapeutic situation.

The pharmaceutical composition can be administered in a convenient manner, such as by injection (e.g., subcutaneous, intravenous, and the like), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition (e.g., enteric coatings are known in the art). The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. The composition will typically be sterile and fluid to the extent that easy syringability exists. Typically the composition will be stable under the conditions of manufacture and storage and preserved against the contaminating action of microorganisms, such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols, such as mannitol, sorbitol, or sodium chloride are used in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the subject's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. "Dosage unit form" as used herein, refers to physically discrete units suited as unitary dosages for the subject to be treated; each unit containing a predetermined quantity of pharmaceutical composition is calculated to produce the desired therapeutic effect in association with the required pharmaceutical carrier. The specification for the dosage unit forms of the disclosure are related to the characteristics of the pharmaceutical composition and the particular therapeutic effect to be achieve.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

The following examples are meant to illustrate, not limit, the disclosed invention.

EXAMPLES

Construction Design and Purification of PTD-DRBD Fusion Proteins pPTD-DRBD was constructed by PCR cloning of PKR DRBD-1 from a human HepG2 cDNA library, followed by insertion into the pTAT vector containing a single N-terminal TAT PTD, HA epitope tag and a C-terminal 6×His purification tag (Wadia et al., 2004). Two additional TAT PTDs were inserted into the N-terminus to yield pPTD-DRBD. To prepare VSVG expressing EGFP-PEST (dGFP) or DsRed-PEST (dDsRed) lenti-virus, pCSC-SP-CW-EGFP-PEST or pCSC-SP-CW-DSRED was constructed from pCSC-SP-CW (Miyoshi et al., 1998) and pd2EGFP-N-1- or pDsRed-Express-DR (BD clontech). For protein expression, BL21 codon plus (DH3) $E.$ $coli$ (Strategene) cells were transformed with pPTD-DRBD, cultured at 37° C. in LB, then at 25° C. for 12 hr after induction with 400 µM IPTG. Cells were recovered by centrifugation for 5 min at 4,500 g, sonicated in Buffer A (20 mM Hepes [pH 7.5], 500 mM NaCl, 5 µg/ml Aprotinin, 1 µg/ml Leupeptin, 0.8 mM PMSF) plus 20 mM imidazole and soluble protein isolated by centrifugation for 15 min at 50,000 g. PTD-DRBD was purified by passage over a Ni-NTA column (Qiagen), followed by loading onto a Mono-S AKAT FPLC in Buffer B (50 mM Hepes [pH 7.5], 20 mM NaCl, 5% glycerol) and eluted in Buffer C (Buffer B plus 1.5 M NaCl). Purified PTD-DRBD was dialyzed against PBS-10% glycerol, flash frozen at 50 µM PTD-DRBD and stored at −20° C.

Cell Culture Conditions. H1299, HaCaT, HFF, B16F0 cells were cultured in 10% FBS-DMEM, antibiotics. T98G cells were cultured in 5% FBS-MEM, antibiotics. Jurkat T cells and Namalwa B cells were cultured in 10% FBS-RPMI, antibiotics. THP-1 macrophage were grown in 10% FBS-RPMI plus 1 mM sodium pyruvate, 4.5 g/L glucose, 50 µM β-mercaptoethanol, antibiotics. The hESC line HUES9 was a kind gift and H9 hESCs were obtained from WiCell. H9 hESCs were grown in 20% knockout serum-DMEM-F12 plus 55 µM βmercaptoethanol, NEAA, Gluta-Max, 4 ng/ml bFGF, antibiotics on murine fibroblast feeder layer. HUES9 hESCs were grown in HUES media (10% knockout serum-DMEM plus 10% Plasmonate, 55 µM β-mercaptoethanol, NEAA, Gluta-Max, 4 ng/ml bFGF, antibiotics) without murine fibroblast feeder layer in media preconditioned for 24 hr on murine fibroblasts. dGFP and dDsRed expressing cells were generated by infection with VSVG expressing dGFP and/or dDsRed lentivirus. VSVG-dGFP and/or VSVG-dDsRed infected cells were isolated by FACS.

PTD-DRBD siRNA Delivery into Cells. A typical PTD-DRBD siRNA delivery reaction mixed 10 µl of 1-5 µM siRNA in water with 10 µl of 10-50 µM PTD-DRBD in PBS-10% glycerol plus 4 µl PBS-10% glycerol on ice for 45 min, diluted 1:5 in media and added to $7.5 \times 10^4$ cells/well in 48 well plate for 6 hr with final siRNA concentrations between 100-400 nM. Cells were then washed with trypsin to remove extracellular PTD-DRBD:siRNA, followed by addition of fresh media plus FBS. Alternatively, cells were simultaneously plated with PTD-DRBD:siRNA for 6 hr, washed in 58 µg/ml heparin sulfate plus media for 10 min, followed by addition of fresh media plus FBS. For Jurkat, Namalwa, THP-1 suspension cells, $2 \times 10^5$ cells were treated with 100-200 nM siRNA:PTDDRBD for 1 hr in media plus 10% Q-serum (5 ml FBS+1 ml Source 30Q resin [Amersham Bioscience], 30 min at RT on mixing platform, followed by 0.22 µm filtration), washed 2× with media, followed by addition of fresh complete media. For H9 and HUES9 hESCs, $6.6 \times 10^5$ cells were treated with 200-400 nM siRNA-PTD-DRBD for 1 hr in serum-free media with no feeder layer, followed by 5 hr in serum-free media on fibroblast feeder layer, then 24 hr with full HUES media plus serum. For siRNA control, cells were treated with 100 nM siRNA in Lipofectamine-2000 (Invitrogen) per the manufacturer's instructions. siRNAs sequences used in this study: EGFP1, EGFP2 (Silencer GFP), GAPDH, Oct-4, Nanog, Sox2, Cdk4 and Silencer Negative control (Ambion); pGL3-luciferase (Luc) and DsRed (Dharmacon); and EGFRvIII (Fan and Weiss, 2005).

Immunoblotting and RT-PCR. $7.5 \times 10^4$ cells/well in 48 well were recovered with trypsin/EDTA, whole cell lysates were prepared in RIPA buffer (1% TritonX-100, 1% Sodium Deoxycholate, 40 mM Tris-HCl, 150 mM NaCl, 0.2% SDS, 5 µg/ml Aprotinin, 1 µg/ml Leupeptin, 0.8 mM PMSF) for 30 min on ice, clarified by centrifugation and proteins resolved by 10% SDS-PAGE. Immunoblot analysis performed on PVDF membranes blocked in 4% skim milk, PBS-T (0.05% PBS, Tween20) for 1 hr at RT, reacted with anti-Oct4 (Santa Cruz), anti-GAPDH (Santa Cruz) antibodies overnight at 4° C., anti-α-tublin (Sigma) antibodies for 1 hr, washed, exposed to HRP conjugated anti-IgG (Santa cruz) antibodies and detected by ECL (Pierce). For GAPDH mRNA Taq-ManTM RT-PCR (Applied Biosystems), 7.5×104 dGFP-H1299 cells/well in 48 well plate were treated as described above with 400 nM GAPDH or control Luciferase siRNA and total RNA isolated at 6, 12, 24, 36, 72 and 96 hr post-addition.

cDNA was synthesized using Oligo-dT and GAPDH mRNA expression was detected using TAQ-MAN probe (Ambion) on 7300 Real time PCR system (Applied Biosystems).

Immunohistochemistry and Flow Cytometry Analysis. Cells were fixed with 4% paraformaldehyde for 30 min at RT, permeabilized in 0.1% TritonX100PBS for 15 min at RT, blocked in 3% skim milk-PBS for 30 min at RT, then reacted with antiOct4 (Santa Cruz), anti-SSEA4 (Santa Cruz) and anti-GATA6 (Santa Cruz) antibodies in 0.1% BSA-PBS overnight at 4° C. Cells were washed and reacted with either Alexa488 or Alexa594 conjugated anti-IgG (Molecular Probes) for 30 min at RT. DNA was counter stained with Hoechst 33342 (Molecular Probes). Cells were analyzed by confocal microscopy (Olympus). For flow cytometry, $1 \times 10^4$ dGFP and/or dDsRed positive cells were analyzed on a FAC-Scan (BD Biosciences) at indicated times.

PTD-dsRNA Binding Domain Fusion Delivery of siRNAs Prior to developing a siRNA delivery strategy three inclusion criterion were established: 1) siRNA delivery into 100% of all cell types (primary or transformed), 2) non-cytotoxic, and 3) siRNA sequence-independent, so that all siRNAs could utilize the approach.

Figure 1:
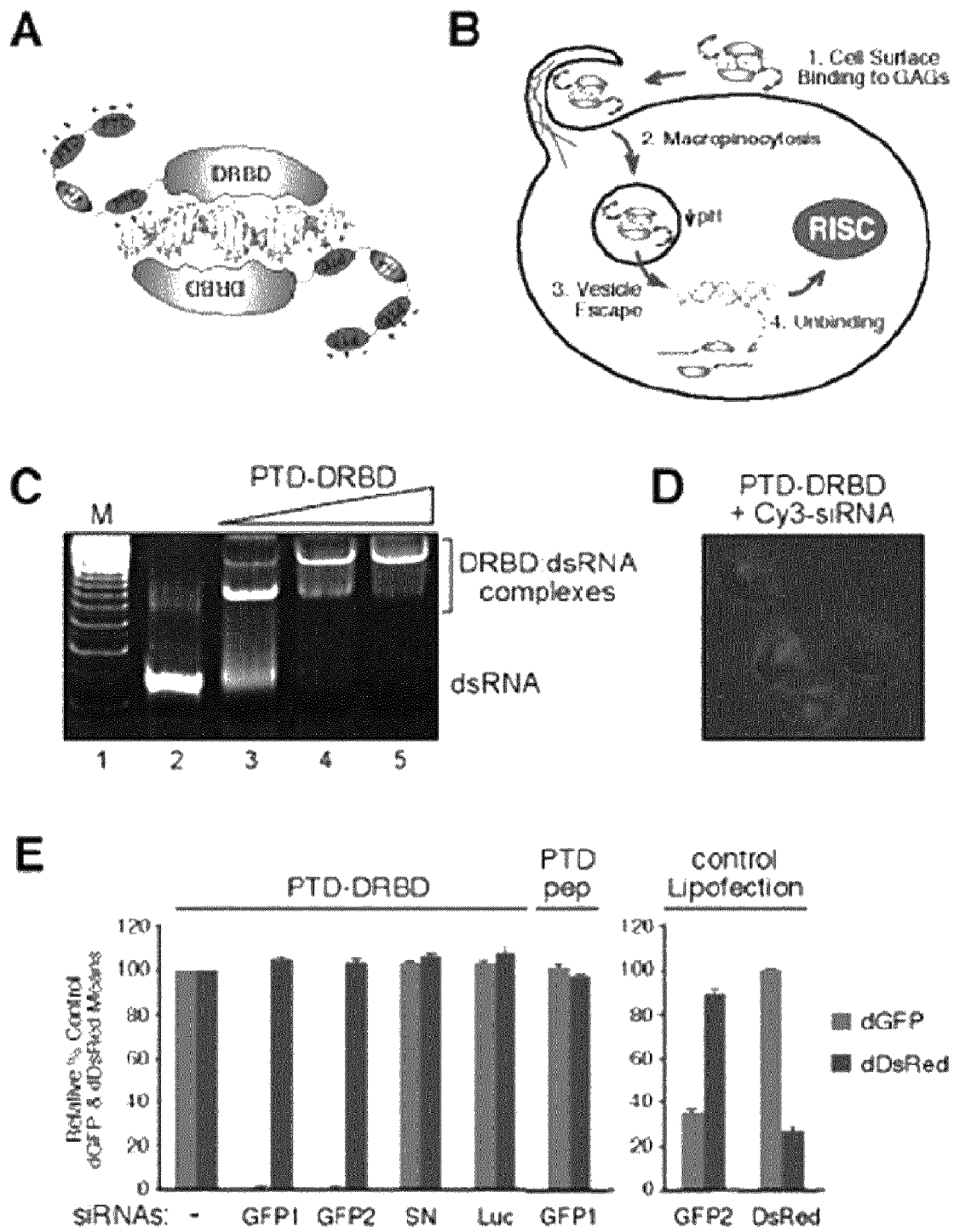
FIG. 1A-E shows PTD-DRBD Mediated Delivery of siRNAs into Cells. (A) Representative cartoon of PTD-DRBD bound to siRNA. DRBDs mask ~16 bp of dsRNA leaving anionic charges on both ends that are hypothesized to be bound by first cationic PTD. (B) Proposed mechanism of PTD-DRBD:siRNA cell entry based on work with TAT-Cre (Wadia et al., 2004). Free cationic PTD domains interact with cell surface anionic proteoglycans (1) inducing macropinocytosis (2), followed by macropinosome pH drop enhancing vesicle escape (3), PTD-DRBD:siRNA cytoplasmic disassembly (4) and siRNA loading into RISC. (C) EMSA analysis of PTD-DRBD bound to Cy3-labeled 19mer siRNA. Two distinct higher order complexes were detected. M, dsDNA ladder marker. (D) Microscopic analysis of H1299 cells treated with PTD-DRBD:siRNA-Cy3 6 hr post-addition. Cells were washed and treated with trypsin/heparin to remove extracellularly bound material prior to microscopy. (E) RNAi knockdown of dGFP and dDsRed by PTD-DRBD:siRNA. H1299 cells co-expressing integrated destabilized dGFP and dDsRed reporter proteins were treated with siRNAs as noted for 6 hr, washed and assayed by flow cytometry at 24 hr post-addition. GFP1 and GFP2 siRNAs are independent sequences; SN, Silencer Negative control siRNA; Luc, Luciferase control siRNA. Mean values are normalized to percent control, error bar indicates SEM, all experiments performed in triplicate.

The proven macromolecular delivery properties of cationic PTDs were used for siRNA delivery. However, to avoid the charge neutralization problem, the PTD was fused to a dsRNA Binding Domain (PTD-DRBD) (FIG. 1A). DRBDs specifically bind to dsRNAs with high avidity by making 2'-OH contacts in two minor grooves, bridging the major groove on 90° surface quadrants of the helix resulting in 4× DBRDs masking ~16 bp dsRNA (Ryter and Schultz, 1998). Numerous PTD-DRBD fusion combinations were generated, purified to homogeneity and tested numerous PTD-DRBD fusion combinations, settling on PTD-PTD-HA tag-PTD-DRBD that was based upon experimental data showing that the unmasked siRNA overhang neutralizes the first and/or second PTD (FIGS. 1A and 1B). Addition of PTD-DRBD to double stranded siRNA resulted in specific and rapid binding of multiple subunits in a concentration dependent fashion (FIG. 1C). The ability of PTD-DRBD to deliver siRNA into cells was examined. Addition of Cy3-labeled siRNA with PTD-DRBD to cells resulted in cellular uptake of siRNAs into all cells in the population, whereas control Cy3-labeled siRNA failed to enter cells (FIG. 1D).

Figure 6:
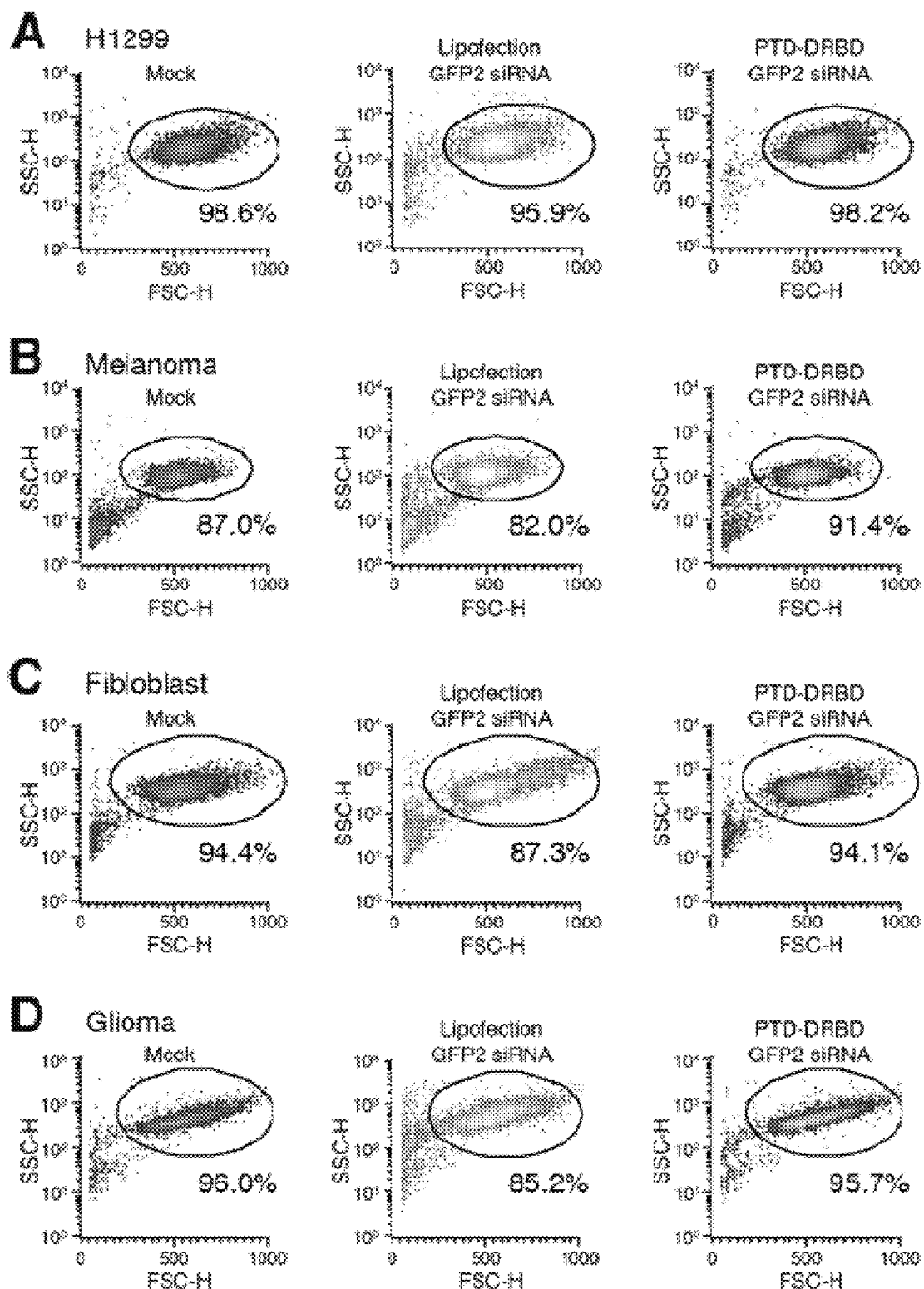

To examine PTD-DRBD delivered siRNA induction of a RNAi response, a human H1299 lung adenocarcinoma reporter cell line was generated containing integrated copies of vectors constitutively expressing destabilized eGFP-PEST (dGFP) and destabilized DsRed-PEST (dDsRed) proteins that have significantly shorter half-lives (~2 hr) than wild type protein (>24 hr). The dGFP/dDsRed integrated reporters allowed for direct determination of single cells, and hence the percentage of cells, undergoing an RNAi response in the population, whereas as other reporters, such as luciferase, or mRNA measurements do not. H1299 dGFP/dDsRed reporter cells were treated with PTD-DRBD, control DRBD, control PTD peptide or control lipofection combined with multiple GFP, DsRed and control siRNAs. siRNA treated reporter cells were analyzed by flow cytometry at 24 hr for expression of dGFP and dDsRed, and cell viability (FIG. 1E, FIG. 6). Importantly, lipofection agents were only used as independent controls and were not used with any PTD-DRBD samples. Addition of PTD-DRBD alone, control PTD peptide or control DRBD (no PTD) in combination with GFP siRNA had no effect on either dGFP or dDsRed expression levels. In contrast, addition of GFP siRNAs plus PTD-DRBD to cells induced a dramatic RNAi knockdown of dGFP with no alteration of internal control dDsRed. Likewise, addition of PTD- DRBD plus DsRed siRNAs resulted in dDsRed knockdown with no alteration of dGFP expression. A total of five sequence-independent GFP siRNAs were tested and all five induced a GFP specific RNAi response with no change of control dDsRed, two are in FIG. 1E. The decrease of dGFP by PTD-DRBD delivered GFP siRNAs was also significantly stronger than control lipofection of GFP siRNAs (FIG. 1E). Addition of PTD-DRBD with two proven RISC loaded control siRNAs, Silencer Negative (SN) and Luciferase (Luc), gave no alteration of either dGFP or dDsRed signal. Little to no alteration of cell viability in PTD-DRBD treated cells was detected, whereas lipofection resulted in measurable cytotoxicity (FIG. 6).

Figure 2:
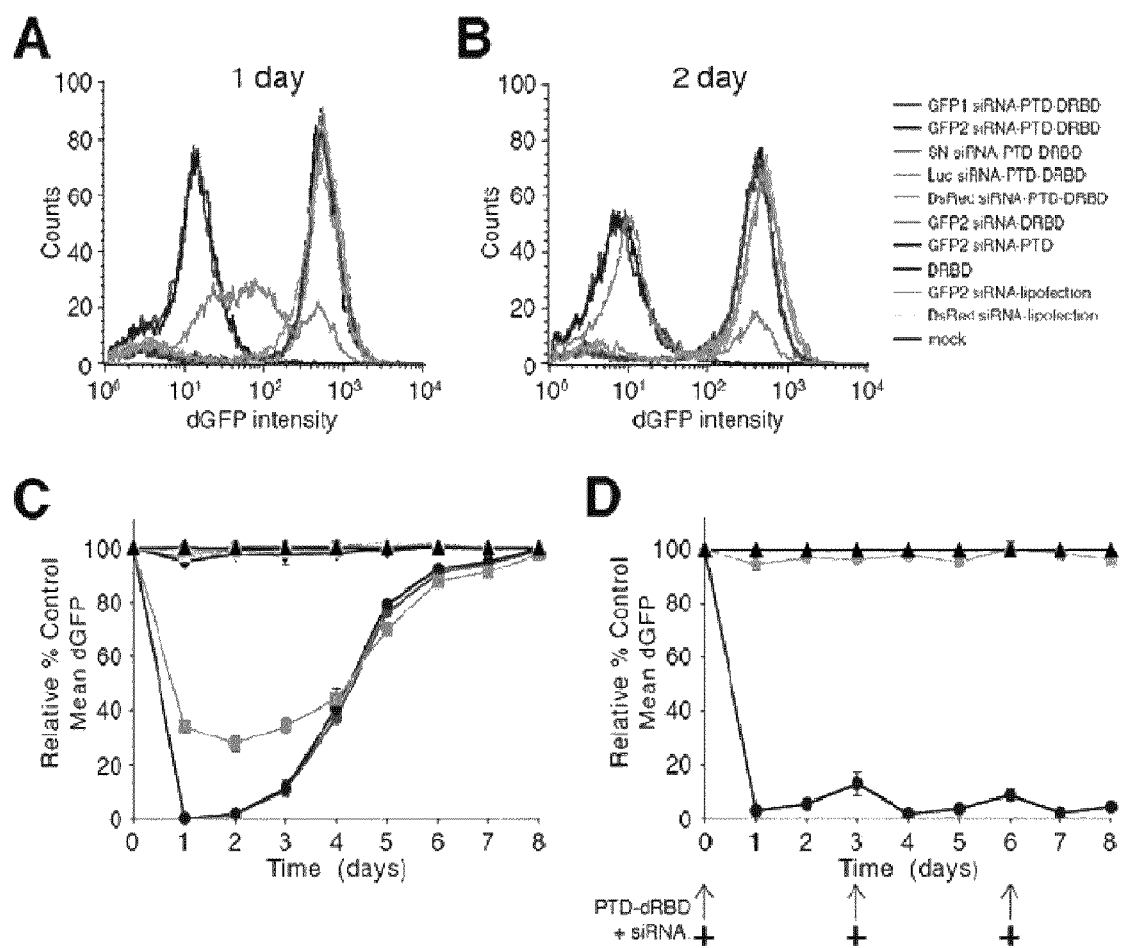
FIG. 2A-D shows the analysis of PTD-DRBD Mediated dGFP RNAi Response (A and B) Flow cytometry single cell histogram analysis of dGFP RNAi response at (A) 1 and (B) 2 days post-treatment of H1299 dGFP/dDsRed cells, as indicated. (C) Flow cytometry analysis of dGFP RNAi knockdown decay kinetics following single siRNA treatment of H1299 dGFP/dDsRed cells. (D) Flow cytometry analysis of dGFP RNAi knockdown decay kinetics following multiple siRNA treatments of H1299 dGFP cells, as indicated. Mean values are normalized to percent control, error bar indicates SEM, all experiments performed in triplicate.

The significantly stronger dGFP RNAi knockdown response by PTD-DRBD vs. lipofection was examined by single cell flow cytometry analysis (FIG. 1E). At 24 hr post-addition, PTD-DRBD delivered dGFP siRNAs had induced a maximal GFP RNAi response in 100% of the cells (FIG. 2A). In contrast, lipofection delivered siRNAs induced an RNAi response that was both incomplete and partially penetrant, with a pool of non-reactive cells that expressed dGFP equal to untreated control cells. At 48 hr, PTD-DRBD delivered GFP siRNAs maintained a complete, 100% RNAi response (FIG. 2B). However, lipofection treated cells resolved further into two distinct populations: a dGFP RNAi responsive population with a similar magnitude of GFP knockdown as PTD-DRBD mediated RNAi and a second population of ~20% of cells that showed no signs of a dGFP RNAi response (FIG. 2B). These observations are entirely consistent with the inability of lipofection to delivery siRNAs into 100% of cells in a population, even in the highly transfectable tumor cells used here, as well as associated cytotoxicities are well appreciated in the field of siRNA delivery.

The kinetics of the RNAi response induced by PTD-DRBD mediated siRNA delivery was examined. H1299 dGFP/dDsRed reporter cells were treated with PTD-DRBD, control PTD peptide or control lipofection combined with multiple GFP, DsRed and control siRNAs then analyzed by flow cytometry daily for 8 days (FIG. 2C). Consistent with the observations above, only PTD-DRBD plus GFP siRNAs induced a dGFP specific RNAi response, whereas all control combinations failed. PTD-DRBD delivered GFP siRNAs maintained a maximal dGFP RNAi between days 1-3 days, followed by a gradual decay to control levels at day 8 (FIG. 2C). With the exception of the limited number of responding cells, control lipofection delivered GFP siRNAs induced a GFP RNAi response with similar induction and decay kinetics as PTD-DRBD delivered siRNAs. The decay curves are entirely consistent with the notion that siRNA loaded RISCs are diluted during cellular division and siRNA half-life. To circumvent the RNAi decay curve, dividing cells were re-treated on days 3 and 6 with PTD-DRBD siRNAs. Repeated treatment resulted in maintenance of the extent and magnitude of the GFP RNAi response measured over 8 days (FIG. 2D). Taken together, these observations demonstrate the ability of PTD-DRBD fusion proteins to efficiently deliver siRNAs into 100% of cells in a non-cytotoxic fashion.

Figure 3:
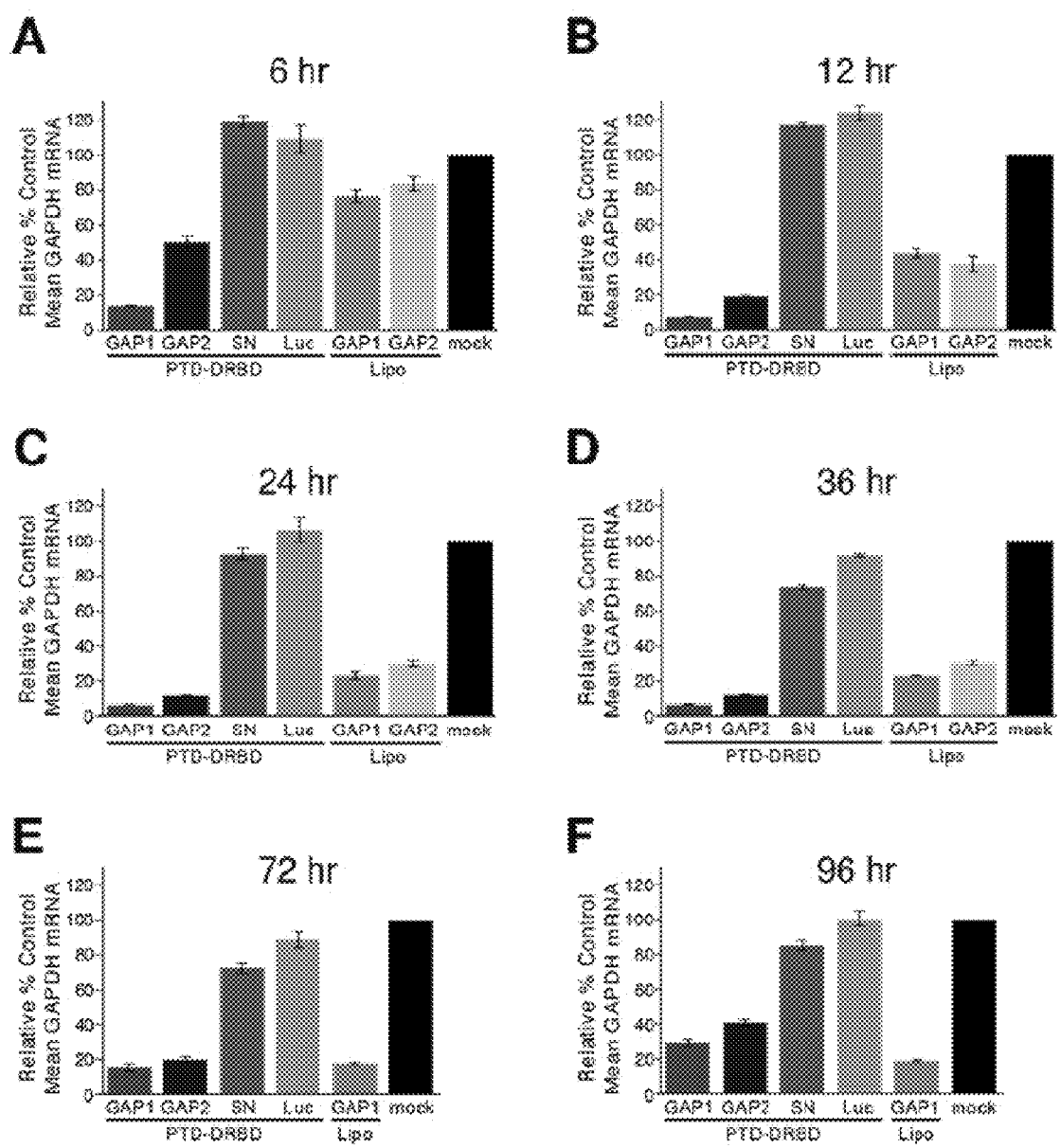
FIG. 3A-F shows knockdown of Endogenous GAPDH mRNA by PTD-DRBD:siRNA. (A-F) Quantitative TaqMan RT-PCR analysis of endogenous GAPDH mRNA expression at 6, 12, 24, 36, 72 and 96 hr post-treatment in H1299 cells, as indicated. Mean values normalized to β2 microglobulin and reported as percent of mock GAPDH control, error bar indicates SEM, all experiments performed in triplicate.

Although the integrated dGFP/dDsRed genes serve as excellent reporter targets for RNAi responses, an endogenous gene was targeted by RNAi, namely GAPDH mRNA, a standard control RNAi target. Treatment of H1299 cells with two sequence-independent GAPDH siRNAs delivered by PTD-DRBD fusions resulted in a GAPDH RNAi response that was first detected at 6 hr post-addition and reached a maximal RNAi response at 12 hr (FIG. 3). In contrast, all PTD-DRBD negative controls failed to induce a GAPDH RNAi response. Interestingly, PTD-DRBD delivered GAPDH siRNAs achieved an RNAi response significantly earlier than control lipofection delivery of the same GAPDH siRNAs, suggesting that PTD-DRBD delivered siRNAs are loaded into RISC more rapidly (FIG. 3). This is entirely consistent with the observed rapid (15 min) detection of LoxP recombination by TAT-Cre addition. Similar to the dGFP RNAi induction and decay kinetics, PTD-DRBD delivered GAPDH siRNA showed a maximal RNAi response out to 72 hr post-treatment followed by a slow decay at 96 hr. Taken together, these observations demonstrate the ability to efficiently target endogenous mRNAs by PTD-DRBD mediated siRNA delivery.

Figure 4:
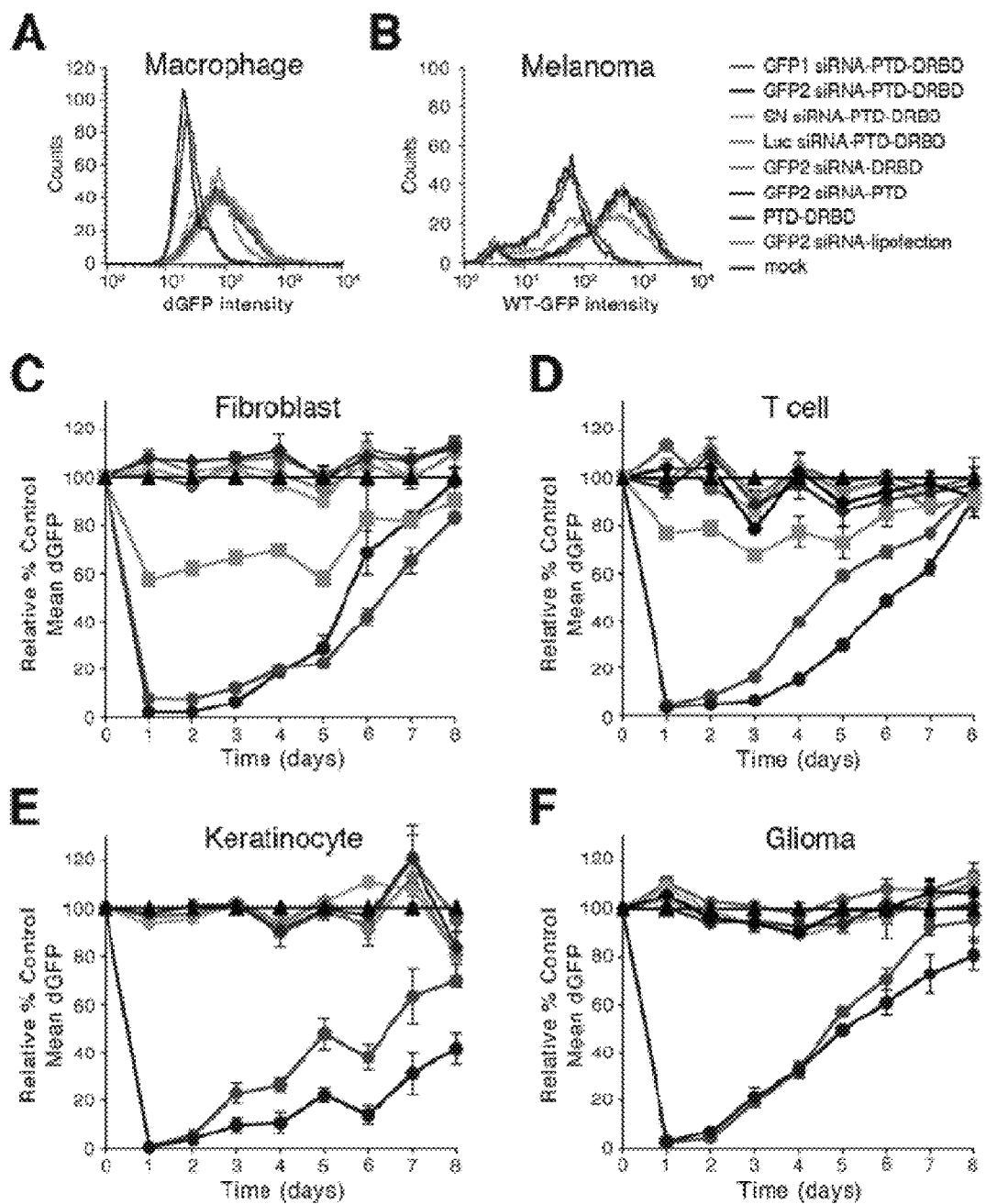
FIG. 4A-F shows PTD-DRBD Delivered siRNA Induces RNAi Response in Wide Variety of Cell Types. (A and B) Flow cytometry single cell histogram analysis of dGFP RNAi response in (A) human THP-1 macrophage cells and wild type eGFP RNAi response in (B) murine B16F0 melanoma cells, as indicated. (C-F) Flow cytometry analysis of dGFP RNAi knockdown decay kinetics following single siRNA treatment of (C) human HFF Primary Fibroblasts, (D) human Jurkat T cells, (E) human HaCaT Keratinocytes, (F) human T98G Glioblastoma cells, as indicated. Mean values are normalized to percent control, error bar indicates SEM, all experiments performed in triplicate.

PTD-DRBD Delivered siRNA Induces an RNAi Response in a Wide Variety of Cell Types. Currently, there is no approach that delivers siRNAs into 100% of all cells. As an example, lipofection delivery of siRNAs is essentially restricted to adherent, highly tumorigenic cells that tolerate significant membrane perturbation. It is poor to completely ineffective on most primary cells and non-adherent hematopoietic lineages, such as T and B cells, macrophages. To explore the possibility of universal siRNA delivery, a dGFP retroviral expression vectors was stably introduced into several primary and tumorigenic cell types (FIG. 4). In contrast to the complete negative results by lipofection, PTD-DRBD delivered siRNAs into macrophage and melanocytes induced a GFP RNAi response in 100% of the population (FIG. 4A). Moreover, PTD-DRBD delivered GFP siRNAs induced complete RNAi responses in adherent primary human fibroblasts, keratinocytes, T cell and glioblastoma cells with similar decay kinetics as H1299 cells (FIG. 4B). In contrast, all negative controls failed to induce a GFP RNAi response. The disclosure demonstrates RNAi responses in all 14 different primary, tumorigenic, adherent and non-adherent cell lines assayed to date (Table 1), suggesting that PTD-DRBD fusions mediate a universal siRNA delivery into cells.

TABLE 1

Summation of all cell lines tested for PTD-DRBD delivery of siRNAs.

| Cell Line | Cell Type | Target Gene |
| --- | --- | --- |
| H9 | Human Embryonic Stem Cell | GFP |
| HUES9 | Human Embryonic Stem Cell | Oct4 Nanog Sox2 |
| H1299 | Human Lung Adenocarcinoma | GFP DsRed GAPDH |
| HFF | Human Primary Fibroblast | GFP |
| T98G | Human Glioma | GFP DsRed |
| U87 | Human Glioma | EGFR-VIII |
| HaCaT | Human Immortal Keratinocyte | GFP |
| HeLa | Human Cervical Carcinoma | GAPDH |
| Jurkat | Human T Cell Leukemia | GFP GAPDH |
| Namalwa | Human Burkitt's B Cell Lymphoma | GFP |
| THP-1 | Human Macrophage/Monocyte | GFP |
| N2a | Murine Immortal Neuronal cells | GFP |
| B16F0 | Murine Melanoma | GFP Cdk4 |
| MEF | Murine Embryonic Fibroblasts | GFP |

Figure 5:
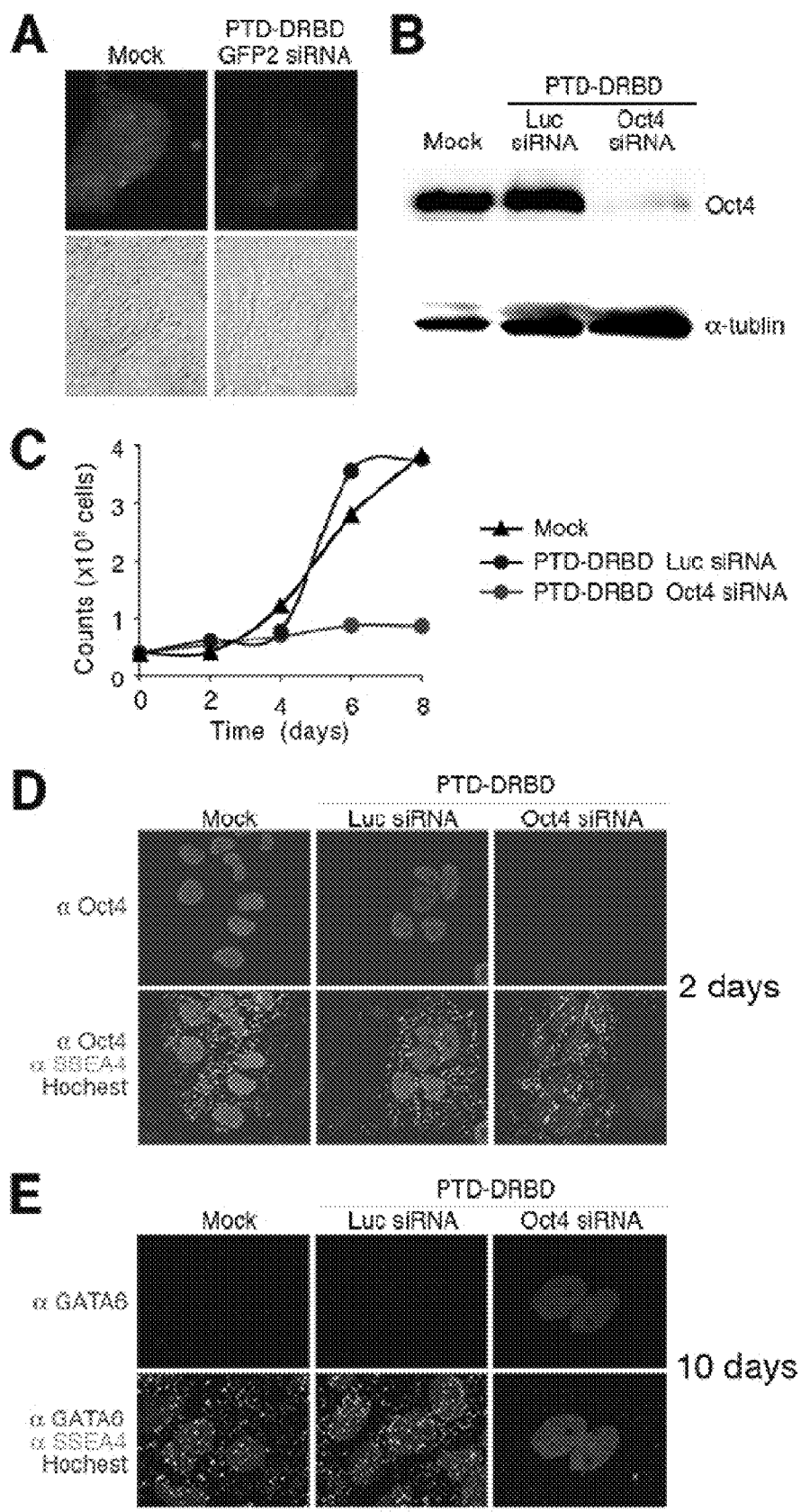
FIG. 5A-E shows PTD-DRBD:siRNA Targeted Differentiation of Human Embryonic Stem Cells. (A) Fluorescent microscopy analysis of human H9 embryonic stem cells expressing wild type eGFP treated with PTD-DRBD GFP2 siRNA at 2 days post-addition. (B) Oct4 immunoblot analysis in HUES9 hESCs treatment with PTD-DRBD Oct4 or control Luciferase (Luc) siRNAs at 2 days post-addition. (C) Cell division curve of human HUES9 embryonic stem cells treated with PTD-DRBD delivered Oct4 or control Luciferase (Luc) siRNAs, as indicated. (D) Immunohistochemistry analysis of Oct4 and SSEA4 expression in HUES9 hESCs at 2 days post-treatment with PTD-DRB delivered Oct4 or Luciferase (Luc) siRNAs. Antibodies: Alexa594-conjugated anti-Oct4

PTD-DRBD Mediated siRNA Delivery in Human Embryonic Stem Cells. Human Embryonic Stem Cells (hESCs) have great potential to treat human disease and RNAi has the potential to direct targeted differentiation of hESCs into mature cell lineages. However, manipulation of hESCs into specific cell lineages by RNAi with the eventual placement into patients will require rigorous protocols that avoid exposure of hESCs to viral vectors and cytotoxic compounds, such as lipofection. Given the efficient and non-cytotoxic siRNA delivery by PTD-DRBD fusions, the ability of PTD-DRBD mediated siRNA was tested to direct hESC differentiation. Using lentiviral infection, a hESC line carrying a wild type eGFP reporter was generated. PTD-DRBD mediated delivery of eGFP siRNAs resulted in a significant decrease in eGFP expression, whereas all controls failed to induce an RNAi response (FIG. 5A). These observations are entirely consistent with the universal delivery aspect of PTD-DRBD mediated siRNA delivery discussed above.

The ability of PTD-DRBD mediated siRNA delivery to affect the fate of hESCs was tested. The Oct4 (PFU5) transcription factor is required to maintain hESC pluripotency and recent reports have shown that Oct4 RNAi knockdown results in hESC differentiation (Boyer et al. 2005; Orkin, 2005). hESC treatment with PTD-DRBD plus Oct4 siRNAs resulted in both an Oct4 specific knockdown and a reduced growth rate, indicative of pluripotency loss and initiation of differentiation (FIGS. 5B,C). In contrast, both mock and control PTD-DRBD plus Luciferase siRNAs did not alter hESC cellular morphology, growth kinetics or Oct4 expression levels. Pluripotent hESCs express multiple cell surface markers, including stage-specific embryonic antigen-4 (SSEA-4) (Henderson et al., 2002). During differentiation into endoderm, hESCs decrease SSEA-4 expression, stop dividing, increase in size and subsequently express the GATA6 differentiation transcription factor (Hay et al., 2004). PTD-DRBD delivered Oct4 siRNAs resulted in loss of Oct4 expression by day 2 with continued SSEA-4 expression (FIG. 5D). However, by 10 days post-treatment, Oct4 siRNA treated cells had lost expression of SSEA-4 and induced expression of the GATA6 endoderm specific transcription factor (FIG. 5E). In contrast, mock and control PTD-DRBD plus Luciferase siRNA treated hESCs did not induce differentiation or alter hESC marker expression (FIG. 5E). Taken together, these observations demonstrate a universal ability of PTD-DRBD fusions to deliver siRNAs and induce specific RNAi responses in a wide variety of primary and tumorigenic cells, to target endogenous genes and to induce hESC differentiation.

siRNA induced RNAi responses are a key experimental procedure for manipulation of cell biology, dissection of genetic pathways, target validation and has great potential for therapeutic intervention. However, due to their macromolecular size (~14,000 Da), and strong anionic charge, siRNAs have no ability to enter cells on their own. Consequently, multiple approaches have been devised to solve the siRNA delivery problem. Cationic lipid transfection reagents are currently the standard siRNA delivery vehicle in vitro. However, this approach as well as other approaches of PEI siRNA condensation, antibody-protamine fusion siRNA condensation, cholesterol LDL particle formation and liposome encapsulation, while promising, fails to target 100% of cells in a population, especially primary cells and hematopoeitic lineages (T and B cells, macrophage). Consequently, there is a significant need for a universal siRNA delivery approach that: 1) targets 100% of all cell types, primary and tumorigenic, adherent and non-adherent, 2) is non-cytotoxic, and 3) that is siRNA sequence-independent.

The PTD-DRBD siRNA delivery approach described here fulfills many of the criterions for a universal siRNA delivery system. First, PTD-DRBD fusions delivered siRNAs into each and every cell type tested, including 14 different primary and tumorigenic, adherent and non-adherent cell types. Second, PTD-mediated siRNA delivery into cells occurs by non-cytotoxic macropinocytosis, a specialized form of fluid phase endocytosis that all cells perform, and therefore does not require expression of high levels of specific receptors. Third, DRBDs bind to dsRNAs (siRNAs) independent of sequence composition and are therefore capable of delivering all siRNAs into cells. Taken together, PTD-DRBD fusions demonstrate a universal siRNA delivery approach into many cell types that are not readily accessible to RNAi manipulation, especially primary cells.

Although a number of embodiments and features have been described above, it will be understood by those skilled in the art that modifications and variations of the described embodiments and features may be made without departing from the teachings of the disclosure or the scope of the invention as defined by the appended claims.

What is claimed is:

1. A composition comprising:
one or more double stranded RNA binding domains (DRBDs) in complex with an RNA interfering agent to form a DRBD-nucleic acid complex; and
a plurality of protein transduction domains (PTD), wherein each of the plurality of PTDs is linked to another PTD, or one or more of the DRBDs of the DRBD-nucleic acid complex or both to render the DRBD-nucleic acid complex cationically charged at a physiological pH, and wherein each DRBD is linked to at least two PTDs.

2. The composition of claim 1, wherein the one or more DRBDs are derived from a polypeptide selected from the group consisting of: PKR, TRBP, PACT, Staufen, NFAR1, NFAR2, SPNR, RHA, NREBP, Kanadaptin, HYL1, hyponastic leaves, ADAR1, ADAR2, ADAR3, TENR, RNaselll, Dicer, RDE-4, FLJ20399, CG1434, CG13139, DGCRK6, CG1800, FLJ20036, MRP-L45, CG2109, CG12493, CG10630, CG17686, and T22A3.5.

3. The composition of claim 1, further comprising a PTD operably linked to the RNA interfering agent.

4. The composition of claim 1, wherein the molar ratio of double-stranded RNA binding protein to nucleic acid is at least 2:1.

5. The composition of claim 1, wherein the plurality of protein transduction domains comprise a PTD derived from a polypeptide selected from the group consisting of a herpesviral VP22 protein; a human immunodeficiency virus (HIV) TAT protein; a homeodomain of an Antennapedia protein (Antp HD), and fragments thereof that function to provide protein transduction.

6. A composition comprising:
a) a first fusion polypeptide comprising:
i) a plurality of protein transduction domains (PTDs), the PTDs comprising a membrane transport function; and
ii) one or more double stranded RNA binding proteins (DRBDs);
b) an RNA interfering agent, wherein the RNA interfering agent is anionically charged and interacts with the one or more DRBDs to form a protein-nucleic acid complex, and wherein the overall anionic charge of the fusion protein-nucleic acid complex is reduced relative to the nucleic acid alone; and
c) a pharmaceutically acceptable carrier wherein the first fusion protein in complex with the RNA interfering agent has a net cationic charge at a physiological pH, and wherein each DRBD is linked to at least two PTDs.

7. The composition of claim 6, wherein the plurality of protein transduction domains are derived from a polypeptide selected from the group consisting of a herpesviral VP22 protein; a human immunodeficiency virus (HIV) TAT protein; a homeodomain of an Antennapedia protein (Antp HD), and fragments thereof that function to provide protein transduction.

8. The composition of claim 6, wherein the RNA interfering agent is a probe used in in situ hybridization.

9. The composition of claim 6, wherein the RNA interfering agent modulates cell proliferation.

10. The composition of claim 9, wherein the modulation inhibits cell proliferation.

11. A method of introducing an anionically charged nucleic acid molecule into a cell comprising contacting the cell with a composition of claim 1 or 6.

12. A method of introducing an RNA interfering agent into a cell comprising:
contacting the cell with a composition comprising one or more double stranded RNA binding domains (DRBDs) in complex with the RNA interfering agent to form a DRBD-nucleic acid complex and wherein the DRBD-nucleic acid complex is linked to a plurality of protein transduction domains (PTD), wherein each of the plurality of PTDs is linked to another PTD, or one or more of the DRBDs of the DRBD-nucleic acid complex or both to render the DRBD-nucleic acid complex cationically charged at a physiological pH, and wherein each DRBD is linked to at least two PTDs.

13. The method of claim 11, wherein the contacting is in vivo or in vitro.

14. The method of claim 12, wherein the contacting is in vivo or in vitro.

15. The method of claim 12, wherein the nucleic acid molecule comprises a dsRNA.

16. The method of claim 12, wherein the dsRNA is processed by the cell to form an siRNA.

17. The method of claim 12, wherein the nucleic acid inhibits thecm production of a target gene product.

18. The method of claim 17, wherein the target gene product causes a cell proliferative disorder.

19. A kit comprising a vessel or vessels containing
(a) one or more double stranded RNA binding domains (DRBDs) each linked to a plurality of protein transduction domains (PTDs), wherein each of the plurality of PTDs is linked to another PTD, or one or more of the DRBDs and wherein in each DRBD is linked to at least two PTDs; and
(b) an RNA interfering agent.

20. The kit of claim 19, wherein the RNA interfering agent is a dsRNA molecule.

21. A method of introducing an RNA interfering agent into a target cell, the method comprising contacting the cell with the composition of claim 1 or 6.

22. The composition of claim 1, wherein the plurality of protein transduction domains comprises at least two different protein transduction domains.

23. The composition of claim 1, wherein the plurality of protein transduction domains comprises two PTDs of HIV-Tat.

24. The composition of claim 23, wherein the plurality of protein transduction domains comprises three PTDs of HIV-Tat.

25. The composition of claim 1, wherein the one or more DRBDs are from PKR.

26. The composition of claim 6, wherein the RNA interfering agent is dsRNA which comprises an siRNA.

27. The composition of claim 6, wherein the RNA interfering agent is 21-23bp in length.

28. The composition of claim 1, wherein the plurality of PTDs comprises a PTD selected from the group consisting of: SEQ ID NO:7 from amino acid 47-57; B1-X1-X2-X3-B2-X4-X5-B3, wherein B1, B2, and B3 are each independently a basic amino acid, the same or different and X1, X2, X3, X4 and X5 are each independently an alpha-helix enhancing amino acid the same or different (SEQ ID NO:1); B1-X1-X2-B2-B3-X3-X4-B4, wherein B1, B2, B3, and B4 are each independently a basic amino acid, the same or different and X1, X2, X3, and X4 are each independently an alpha-helix enhancing amino acid the same or different (SEQ ID NO:2); X-X-R-X-(P/X)(B/X)-B-(P/X)-X-B-(B/X), wherein X is any alpha helical promoting residue such as alanine; P/X is either proline or X as previously defined, B is a basic amino acid residue and B/X is either B or X as defined above (SEQ ID NO:4); a sequence of about 7 to 10 amino acids and containing KX1RX2X1, wherein X1 is R or K and X2 is any amino acid (SEQ ID NO:5); RKKRRQRRR (SEQ ID NO:6); and KKRPKPG (SEQ ID NO:3).

29. A composition comprising:
at least one fusion protein selected from the group consisting of:
(i) a DRBD-single PTD fusion protein consisting of a double stranded RNA binding domain (DRBD) linked to one protein transduction domain; and
(ii) a DRBD-multi-PTD fusion protein consisting of a DRBD and a plurality of PTDs linked to the DRBD;
wherein the DRBD is in complex with an RNA interfering agent to form a DRBD-nucleic acid complex.

30. A composition consisting of:
at least one fusion protein selected from the group consisting of:
(i) a DRBD-single PTD fusion protein consisting of a double stranded RNA binding domain (DRBD) linked to one protein transduction domain; and
(ii) a DRBD-multi-PTD fusion protein consisting of a DRBD and a plurality of PTDs linked to the DRBD;
an RNA interfering agent in complex with the DRBD to form a DRBD-nucleic acid complex.

* * * * *

SEQUENCE LISTING

```
<160> NUMBER OF SEQ ID NOS: 15

<210> SEQ ID NO 1
<211> LENGTH: 8
<212> TYPE: PRT
<213> ORGANISM: Artificial Sequence
<220> FEATURE:
<223> OTHER INFORMATION: Artificial Peptide consensus sequence
<220> FEATURE:
<221> NAME/KEY: misc
<222> LOCATION: (1)..(1)
<223> OTHER INFORMATION: X at position 1 is a basic amino acid
<220> FEATURE:
<221> NAME/KEY: misc
<222> LOCATION: (2)..(4)
<223> OTHER INFORMATION: X is any alpha-helix enhancing amino acid
<220> FEATURE:
<221> NAME/KEY: misc
<222> LOCATION: (5)..(5)
<223> OTHER INFORMATION: X at position 5 is a basic amino acid
<220> FEATURE:
<221> NAME/KEY: misc
<222> LOCATION: (6)..(7)
<223> OTHER INFORMATION: X is any alpha-helix enhancing amino acid
<220> FEATURE:
<221> NAME/KEY: misc
<222> LOCATION: (8)..(8)
<223> OTHER INFORMATION: X at position 8 is a basic amino acid
```

```
<400> SEQUENCE: 1

Xaa Xaa Xaa Xaa Xaa Xaa Xaa Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: Artificial Peptide consensus sequence
<220> FEATURE:
<221> NAME/KEY: misc
<222> LOCATION: (1)..(1)
<223> OTHER INFORMATION: X at position 1 is a basic amino acid
<220> FEATURE:
<221> NAME/KEY: misc
<222> LOCATION: (2)..(3)
<223> OTHER INFORMATION: X is any alpha-helix enhancing amino acid
<220> FEATURE:
<221> NAME/KEY: misc
<222> LOCATION: (4)..(5)
<223> OTHER INFORMATION: X at position 4 and 5 are each independently
      a basic amino acid
<220> FEATURE:
<221> NAME/KEY: misc
<222> LOCATION: (6)..(7)
<223> OTHER INFORMATION: X is any alpha-helix enhancing amino acid
<220> FEATURE:
<221> NAME/KEY: misc
<222> LOCATION: (8)..(8)
<223> OTHER INFORMATION: X is a basic amino acid

<400> SEQUENCE: 2

Xaa Xaa Xaa Xaa Xaa Xaa Xaa Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Artificial peptide sequence

<400> SEQUENCE: 3

Lys Lys Arg Pro Lys Pro Gly
1               5

<210> SEQ ID NO 4
<211> LENGTH: 11
<212> TYPE: PRT
<213> ORGANISM: Artificial Sequence
<220> FEATURE:
<223> OTHER INFORMATION: Artificial Peptide consensus sequence
<220> FEATURE:
<221> NAME/KEY: misc
<222> LOCATION: (1)..(2)
<223> OTHER INFORMATION: X is any alpha-helix enhancing amino acid
<220> FEATURE:
<221> NAME/KEY: misc
<222> LOCATION: (4)..(4)
<223> OTHER INFORMATION: X is any alpha-helix enhancing amino acid
<220> FEATURE:
<221> NAME/KEY: misc
<222> LOCATION: (5)..(5)
<223> OTHER INFORMATION: X is any alpha-helix enhancing amino acid or
      a proline
<220> FEATURE:
<221> NAME/KEY: misc
<222> LOCATION: (6)..(7)
<223> OTHER INFORMATION: X is any alpha-helix enhancing amino acid or
      a basic amino acid
<220> FEATURE:
<221> NAME/KEY: misc
<222> LOCATION: (8)..(8)
```

```
<223> OTHER INFORMATION: X is any alpha-helix enhancing amino acid or
      a proline
<220> FEATURE:
<221> NAME/KEY: misc
<222> LOCATION: (9)..(9)
<223> OTHER INFORMATION: X is any alpha-helix enhancing amino acid
<220> FEATURE:
<221> NAME/KEY: misc
<222> LOCATION: (10)..(11)
<223> OTHER INFORMATION: X is any alpha-helix enhancing amino acid or
      a basic amino acid

<400> SEQUENCE: 4

Xaa Xaa Arg Xaa Xaa Xaa Xaa Xaa Xaa Xaa
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Artificial Peptide consensus sequence
<220> FEATURE:
<221> NAME/KEY: misc
<222> LOCATION: (2)..(2)
<223> OTHER INFORMATION: X is arginine or lysine
<220> FEATURE:
<221> NAME/KEY: misc
<222> LOCATION: (4)..(4)
<223> OTHER INFORMATION: X is any amino acid
<220> FEATURE:
<221> NAME/KEY: misc
<222> LOCATION: (5)..(5)
<223> OTHER INFORMATION: X is an arginine or lysine

<400> SEQUENCE: 5

Lys Xaa Arg Xaa Xaa
1               5

<210> SEQ ID NO 6
<211> LENGTH: 9
<212> TYPE: PRT
<213> ORGANISM: Artificial Sequence
<220> FEATURE:
<223> OTHER INFORMATION: Artificial Peptide Sequence

<400> SEQUENCE: 6

Arg Lys Lys Arg Arg Gln Arg Arg Arg
1               5

<210> SEQ ID NO 7
<211> LENGTH: 86
<212> TYPE: PRT
<213> ORGANISM: Human immunodeficiency virus type 1

<400> SEQUENCE: 7

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85
```

```
<210> SEQ ID NO 8
<211> LENGTH: 5
<212> TYPE: PRT
<213> ORGANISM: Artificial Sequence
<220> FEATURE:
<223> OTHER INFORMATION: Peptide Linker Sequence

<400> SEQUENCE: 8

Gly Gly Gly Gly Ser
1               5

<210> SEQ ID NO 9
<211> LENGTH: 6
<212> TYPE: PRT
<213> ORGANISM: Artificial Sequence
<220> FEATURE:
<223> OTHER INFORMATION: Peptide Linker Sequence
<220> FEATURE:
<221> NAME/KEY: misc
<222> LOCATION: (6)..(6)
<223> OTHER INFORMATION: X is a repeat of GGGGS one or more times

<400> SEQUENCE: 9

Gly Gly Gly Gly Ser Xaa
1               5

<210> SEQ ID NO 10
<211> LENGTH: 12
<212> TYPE: PRT
<213> ORGANISM: Artificial Sequenc
<220> FEATURE:
<223> OTHER INFORMATION: Peptide Linker Sequence

<400> SEQUENCE: 10

Gly Lys Ser Ser Gly Ser Gly Ser Glu Ser Lys Ser
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Peptide Linker Sequence

<400> SEQUENCE: 11

Gly Ser Thr Ser Gly Ser Gly Lys Ser Ser Glu Gly Lys Gly
1               5                   10

<210> SEQ ID NO 12
<211> LENGTH: 18
<212> TYPE: PRT
<213> ORGANISM: Artificial Sequence
<220> FEATURE:
<223> OTHER INFORMATION: Peptide Linker Sequence

<400> SEQUENCE: 12

Gly Ser Thr Ser Gly Ser Gly Lys Ser Ser Glu Gly Ser Gly Ser Thr
1               5                   10                  15

Lys Gly

<210> SEQ ID NO 13
<211> LENGTH: 18
```

```
<212> TYPE: PRT
<213> ORGANISM: Artificial Sequence
<220> FEATURE:
<223> OTHER INFORMATION: Peptide Linker Sequence

<400> SEQUENCE: 13

Gly Ser Thr Ser Gly Ser Gly Lys Pro Gly Ser Gly Glu Gly Ser Thr
1               5                   10                  15

Lys Gly

<210> SEQ ID NO 14
<211> LENGTH: 14
<212> TYPE: PRT
<213> ORGANISM: Artificial Sequence
<220> FEATURE:
<223> OTHER INFORMATION: Peptide Linker Sequence

<400> SEQUENCE: 14

Glu Gly Lys Ser Ser Gly Ser Gly Ser Glu Ser Lys Glu Phe
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Peptide sequence of protamine fragment

<400> SEQUENCE: 15

Arg Ser Arg Arg Arg Arg Arg Arg Ser Cys Gln Thr Arg Arg Arg
1               5                   10                  15
```